United States Patent [19]

Ma

[11] Patent Number: 5,394,876
[45] Date of Patent: Mar. 7, 1995

[54] METHOD AND APPARATUS FOR AIMING A DOPPLER FLOW SENSING DEVICE

[75] Inventor: Qinglin Ma, Bothell, Wash.

[73] Assignee: SpaceLabs Medical, Inc., Redmond, Wash.

[21] Appl. No.: 268,847

[22] Filed: Jun. 30, 1994

[51] Int. Cl.⁶ ............................................. A61B 8/00
[52] U.S. Cl. ............................................. 128/661.09
[58] Field of Search ...................... 128/661.08, 661.09, 128/661.10, 662.04, 916, 660.05

[56] References Cited

U.S. PATENT DOCUMENTS

| | | | |
|---|---|---|---|
| 5,085,220 | 2/1992 | Nudell et al. | 128/661.09 |
| 5,329,929 | 7/1994 | Sato et al. | 128/661.09 |
| 5,339,816 | 8/1994 | Akamatsu et al. | 128/661.09 |

*Primary Examiner*—George Manuel
*Attorney, Agent, or Firm*—Seed and Berry

[57] ABSTRACT

A method and apparatus for aiming a pulse Doppler flow sensing device are presented. The Doppler flow device transmits ultrasonic energy in a wide beam which uniformly encompasses a blood vessel and receives the reflected ultrasonic energy in the same wide beam and also in a beam which is small enough to be placed within the blood vessel. When the beams are concentric with the blood vessel, the device is correctly placed. A processor/controller process the received reflected Doppler energy and calculates the maximum and mean blood velocities from both beams. It also tests whether the blood velocities satisfy predetermined criteria. If the criteria are satisfied, the Doppler device is properly aligned with the blood vessel and the measurement is valid.

33 Claims, 12 Drawing Sheets

METHOD AND APPARATUS FOR AIMING A DOPPLER FLOW SENSING DEVICE

TECHNICAL FIELD

This invention relates to a method and apparatus for aiming a Doppler flow sensor, and more particularly, to a method and apparatus for centering the Doppler flow sensor on the vessel carrying the flow.

Background Art

This invention will facilitate the aiming of Doppler flowmeters which are based on the art described by Hottinger (in U.S. Pat. No. 4,431,936), Fu et al. (in "Annular Arrays for Quantitative Pulsed Doppler Ultrasonic Flowmeters," ULTRASONIC IMAGING, 5, pp. 1-16, 1983, U.S. Pat. Nos. 4,067,236 and 4,519,260), Skidmore et al. (in U.S. Pat. No. 4,807,636) and Nudell et al. (in U.S. patent application Ser. No. 07/417,525). The flowmeters disclosed in these patents measure volume blood flow in biological vessels, such as the aorta.

Simple Doppler velocimeters have not been routinely adopted as cardiac output devices for several reasons. One important reason is that they cannot provide accurate flow measurements when they are not used in conjunction with an imaging device that provides accurate Doppler angle.

Simple velocimeters have suffered from several other theoretical drawbacks in their role as cardiac output devices. First, the velocity measurements that they make can incorrectly estimate the true lumenal velocity because the velocity they measure is a function of the cosine of the angle of incidence of the ultrasonic beam relative to flow, and this angle is only known to a limited degree of accuracy. Second, most commercially available devices generate beams which are not wide enough to uniformly insonify the breadth of the aortic lumen. As a result, there is uncertainty as to the relationship between the measured and true mean lumenal velocity. Third, clinicians have had difficulty in unambiguously aligning the Doppler sample volume With the center of the aorta. This has been a particularly troublesome aspect of Continuous wave (CW) velocimeters, which create an axially large sample volume and, consequently, can easily interrogate vessels other than the aorta (particularly the innominate artery) from the suprasternal notch.

The existing methods to identify the correct placement of the incident beam with the aorta without an imager fall into two categories: the first is to listen for the highest pitched aortic blood flow sound from the audio signal, and the other is to maximize the received backscattered power from the red blood cells. The difficulties caused by the audio signal method are 1) the variability in the ability of different operators to identify the high frequency sound and (2) the insufficient resolution of the human ear when the flow profile is close to that of a plug flow (i.e., having an essentially constant velocity across the entire aorta). One disadvantage for the backscattered power method is that the backscattered power received by the transducer is affected by the constantly moving organs, the sternal bone, gas bubbles in the couplant, an inhomogeneous acoustic environment, and other factors unrelated to the flow velocity in the aorta. While these existing methods may be sufficient for qualitative measurement, they are not satisfactory for quantitative measurement. The biggest disadvantage for both methods is that they all depend on the operator's subject judgment based on the skill and training of the individual user.

Clinical research has recently demonstrated the accuracy of a noninvasive cardiac output device which is based upon the attenuation compensated volume flowmeter (ACVF) principle first described by Hottinger. See, for example, *Determination of cardiac output in critically ill patients by dual beam Doppler echocardiograph*, JACC, v. 13, No. 2, pp. 340-37, 1989, by Looyenga et al. The Hottinger principle calls for the simultaneous generation of two overlapping Doppler sample volumes. A narrow sample volume must reside wholly within moving blood, while a wider sample volume must uniformly insonify a cross-sectional slice of the relevant blood Vessel. According to the Hottinger principle, the wide and narrow beams cannot be properly centered over the blood vessel unless the power received through both the wide and narrow beams is maximized.

However, maximization of the wide and narrow powers may not necessarily result in acceptable centering of the wide and narrow beams. Depending upon the thoroughness Of the search performed by the operator, the narrow and wide beams may never be brought through the center of the aortic lumen. Without traversing the center of the lumen, wide and narrow power will be maximized in a position that does not necessarily fulfill the Hottinger requirements for sample volume placement.

The primary impediment to the widescale commercial acceptance of such devices is the practical difficulty operators have in aligning the Doppler sample volumes with the aortic lumen. In addition, no reliable criteria based upon velocity and power have been developed which allow clinicians to unambiguously know that Hottinger-type flowmeters are properly aligned relative to the biological lumen in question. Aiming of ACVF devices is exacerbated by the fact that it is difficult to make wide and narrow sample volumes which are respectively wide and narrow enough to easily accommodate the largest and smallest adult aortic lumens. The wide sample volume is often just large enough to uniformly insonify large aortas and the narrow sample volume is often just small enough to fit within the smallest aortic lumens.

DISCLOSURE OF THE INVENTION

It is an object of the present invention to provide a method and apparatus for aiming Doppler velocimeters.

This invention will be particularly useful with a pulsed Doppler sensor. For cardiac measurement, the optimized frequency range is 2 to 4 MHz. It is expected that this invention will be particularly well-suited to be applied in a Hottinger-type, non-invasive cardiac output monitor. However, it may be suitable for use in other monitor types, as well.

According to one aspect, the invention is an apparatus for aiming a sensor for detecting the flow of a fluid through a vessel at an interrogation depth in a body. The apparatus comprises transmit means, receive means, and processing means. The transmit means transmits a pulse of energy into the body. The receive means receives the energy reflected in a wide area from an interrogation depth and produces a first receive signal in response thereto and for receives the energy reflected in a narrow area from the interrogation depth and produces a second receive signal in response thereto, the narrow area being encompassed by the wide area. The processing means processes the first receive signal and produces a mean wide velocity value ($V_{mean}^W$) and a maximum wide velocity value ($V_{max}^W$) therefrom. If also processes the second receive signal and produces a mean narrow velocity value ($V_{mean}^N$) and a maximum narrow velocity value ($V_{max}^N$) therefrom. The processing means further processes $V_{mean}^W$, $V_{max}^W$, $V_{mean}^N$, and $V_{max}^N$ and produces an indication signal indicating whether the narrow beam is confined within the vessel at the interrogation depth and the wide beam confines the vessel at the interrogation depth.

According to another aspect, the invention is a method for aiming a sensor for detecting the flow of a fluid through a vessel at an interrogation depth in a body. The method comprises the steps of (a) transmitting a pulse of energy into the body, (b) receiving the energy reflected in a wide area from an interrogation depth and producing a first receive signal in response thereto, and (c) receiving the energy reflected in a: narrow area from the interrogation depth and producing a second receive signal in response thereto, the narrow area being encompassed by the wide area. The method further comprises the steps of (d) processing the first receive signal and producing a mean wide velocity value ($V_{mean}^w$) and a maximum wide velocity value ($V_{max}^W$)therefrom, (e) processing the second receive signal and producing a mean narrow velocity value ($V_{mean}^n$) and a maximum narrow velocity value ($V_{max}^n$) therefrom, and (f) processing $V_{mean}^W$, $V_{max}^W$, $V_{mean}^n$, and $V_{max}^n$ and producing an indication signal indicating whether the narrow beam is confined within the vessel at the interrogation depth and the wide beam confines the vessel at the interrogation depth.

BRIEF DESCRIPTION OF THE DRAWINGS

FIGS. 6A-C are schematic representations of various situations which can be encountered when operating with a sensor producing wide and narrow ultrasonic beams, as shown in FIG. 2.

BEST MODES FOR CARRYING OUT THE INVENTION

Figure 1A:
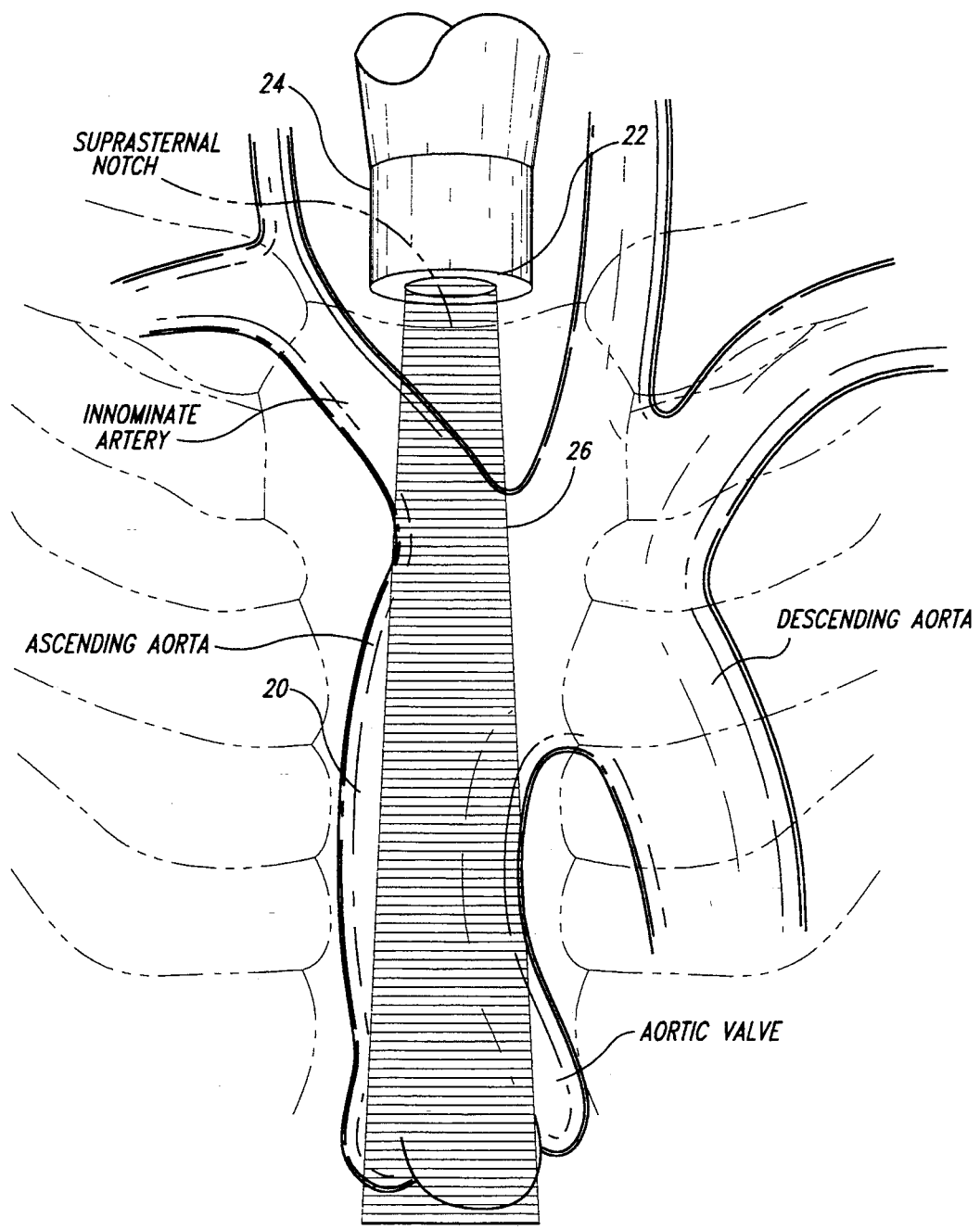
FIG. 1A is an anterior view of a human thorax.

To obtain an accurate measurement of blood flow based on the Doppler principle, it is necessary to know the location of the insonification beam relative to the blood flow profile. Specifically, the algorithm identifies heart beats in which the insonification beam from the suprasternal notch has the minimum incident angle with the ascending aortic blood flow profile. If the incidence angle is unknown, it is best to minimize the angle, because the smaller the angle the more accurate the measurement of velocity. The existing Doppler principle methods cannot achieve the results within the required error range for the aortic cross-sectional area measurement.

A method which can objectively identify the correct alignment of the insonification beam with the blood vessel on a beat-to-beat basis is particularly useful. The method presented herein uses an algorithm which identifies the heart beats in which the ultrasonic beam is close to the correct placement with the aortic blood flow profile and the apparatus implements the algorithm. Blood flow velocity is a function of both time and space. The velocity at a given moment or averaged over a certain time period varying across the vessel lumen is called the velocity profile, while that at a given location or spatially averaged over the vessel cross-sectional area varying with time is called the velocity waveform. Flow has been classified into several forms such as laminar, turbulent, steady, sinusoidal, and pulsatile. Of these, pulsatile flow is the most appropriate type to be applied to the study of the aortic flow, even though there may be turbulence and the blood vessel is not an infinitely long rigid tube.

The algorithm was derived from the results of theoretical and experimental studies of the pulsatile flow of blood through a blood vessel. First, Womersley's pulsatile flow theory "Oscillatory Motion of a Viscous Liquid in a Thin-walled Elastic Tube—I. The Linear Approximation for Long Waves," PHIL. MAG., 46 pp. 199–205, 1955) was used to obtain the aortic flow profile from the in vivo mean velocity waveform. Next, the predicted mean velocity was compared with the in vivo data and the algorithm developed, based on the study of the aortic flow profile. Finally, the algorithm was used to analyze the in vivo aortic flow data and compared with aiming results obtained without using the algorithm.

Womersley and Lambossy (in "Oscillations forcees d'un liquide incompressible et fisqueux dan tube rigide et horizontal," Calcul de la force de frottement, HELV. ACTA 25, 371–383, 1952) independently developed the pulsatile flow theory which describes the oscillatory flow in an infinitely long rigid tube due to a simple harmonic pressure gradient based on the fluid dynamics. Later, D. J. Evans (in *Measurement of Blood Flow Volume Rate by Doppler Ultrasound*, University of Bristol, 1984) obtained the mathematical expressions which describe a pulsatile flow, using Womersley's theory. The basic idea is that a pulsatile flow waveform is composed of many oscillatory flow components represented by the Fourier series components of the waveform. The overall velocity profile is a summation of the contributions from all the simple sinusoidal components. If a mean velocity waveform V(t) is obtained by a uniform beam which is wide enough to encompass the whole cross section of the vessel, it is expanded into Fourier series:

$$V(t) = \frac{V_o}{2} + \sum_{p=1}^{\infty} V_p \cos(p\omega t - \phi_p),$$

where $$V_p = \sqrt{a_p^2 + b_p^2}, \phi_p = \arctan(b_p/a_p), \omega = \frac{2\pi}{T},$$

$$a_p = \frac{2}{T} \int_0^T V(t)\cos(p\omega t)dt, b_p = \frac{2}{T} \int_0^T V(t)\sin(p\omega t)dt,$$

In accordance with Womersley's theory, the overall velocity profile is given by:

$$U(y) = \{2V_0(1 - y^2) + \sum_{p=1}^{\infty} V_p|\psi_p| \cos(p\omega t - \phi_p + \chi_p)\}$$

where $$\psi_p = \frac{\tau_p[J_0(\tau_p) - J_0(y\tau_p)]}{\tau_p J_0(\tau_p) - 2J_1(\tau_p)} = |\psi_p|\exp(i\chi_p),$$

$$\tau_p = \alpha_p i^{3/2}, \alpha_p = R\left(\frac{\omega_p}{v}\right)^{\frac{1}{2}} = R\left(\frac{2\pi p}{Tv}\right)^{\frac{1}{2}},$$

where
R is the vessel radius,
v is the kinematic viscosity,
y is the non-dimensional radial coordinate r/R,
$J_0(x)$ is the first-kind zero's order Bessel function,
$J_1(x)$ is the first-kind first order Bessel function.

Figure 1B:
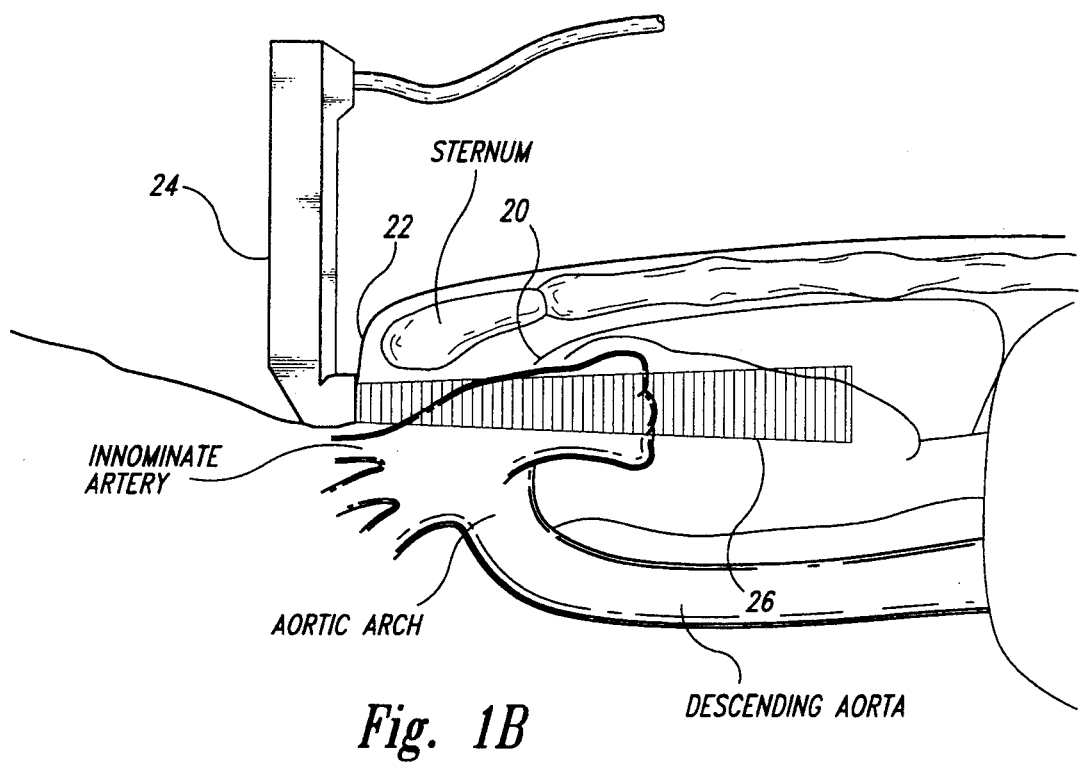
FIG. 1B is a sagittal view of a human thorax.

The relevant anatomical details of the circumstances under which the invention is used are shown in FIGS. 1A and 1B. FIGS. 1A and 1B are respectively anterior and sagittal views of a human torso. The Doppler measurements on which the method is based are obtained from the forward blood flow in the ascending aorta 20, which emanates from the left ventricle of the heart (not shown) and is typically circular in cross section. The suprasternal notch 22 provides an acoustic window for the measurement of the blood flow in the ascending aorta 20. A simple pulsed wave and continuous wave Doppler device such as ultrasonic transducer 24 located in the suprasternal notch 22 can be used to measure the velocity of forward moving blood in the ascending aorta 20. The transducer 24 projects a beam 26 of ultrasonic energy which propagates substantially along the axis of the ascending aorta 20. When these measurements are combined with the measurement of the aortic cross-sectional area, cardiac output can be calculated.

Figure 2:
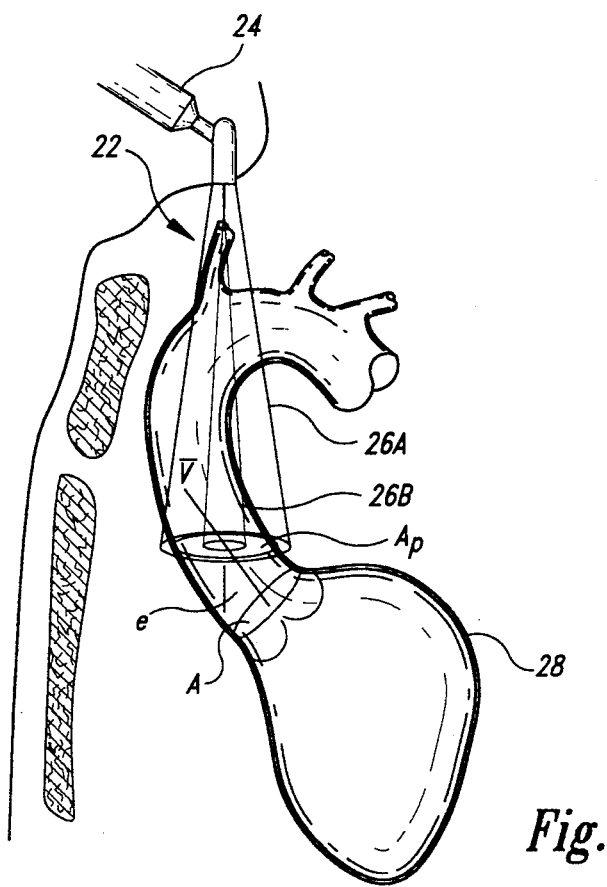
FIG. 2 is a schematic,view of a typical insonification profile of an aorta with a sensor producing wide and narrow ultrasonic beams.

FIG. 2 is a schematic view of the interrogation profile of an ACVF device aimed at the ascending aorta 20. The transducer 24 transmits ultrasonic energy in a wide beam 26A and receives the returning ultrasonic energy according to the wide beam 26A and a narrow beam 26B. It has been known in the prior art to measure the cardiac output of the heart 28 through the ascending aorta 20 from measurements of the mean velocity V and the cross section area A. In this prior art method, the Doppler signal derived from the wide beam 26A is used to obtain a mean velocity estimate, and the ratio of the Doppler power present in the wide and narrow beams 26A and 26B is used to obtain an estimate of the projected aortic area. Multiplication of the two terms yields the instantaneous flow rate. However, this method is highly dependent upon the wide and narrow beams 26A and 26B being correctly placed relative to the ascending aorta 20. The present method implements criteria which can guide the establishment of correctly placed wide and narrow beams 26A and 26B.

Figure 3:
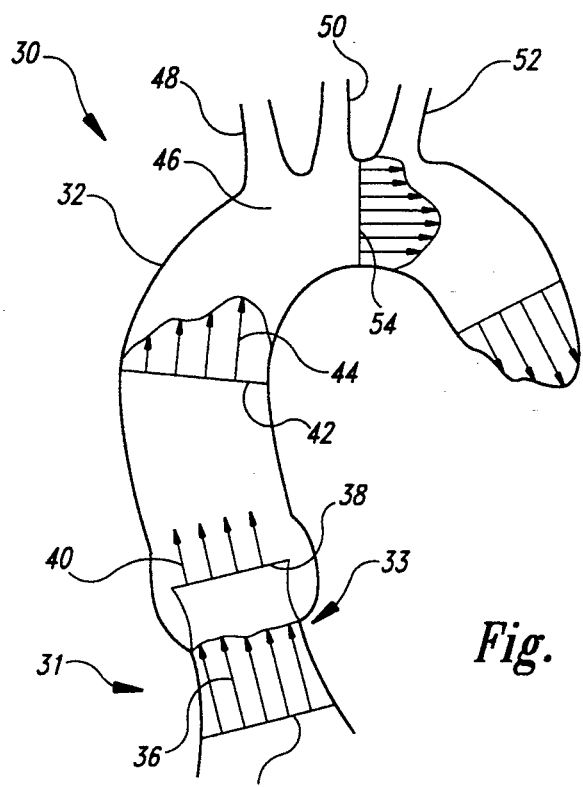
FIG. 3 is a view of the blood flow velocity profiles expected in the aorta when no dilation of the ascending aorta is present.

FIG. 3 is a view of the blood flow velocity profiles expected in a normal aorta 30 and the left ventricular outflow tract 31 when no dilation of the ascending aorta is present. The aorta 30 is defined by a wall 32. The blood velocity profile at station 34 at the aortic orifice 33 is indicated by the array of arrows 36 which show the direction and magnitude of the velocity of the blood as a function of transverse position at station 34. The fact that the blood velocity at station 34 is substantially constant, even very close to the wall 32, is indicated by the series of parallel, equal-length arrows 32. The blood velocity profile at station 38, which is located downstream from station 34, is indicated by arrows 40. At station 38, the blood velocities nearest the wall 32 are lower than those in the center of the aorta 30, and, at the beginning of the aortic arch 46, the velocity is maximum near the inner curvature Of the aorta 30. This skewing effect is seen even more clearly at station 42, where the innermost of the arrows 44 indicates that the maximum blood velocity is nearest the inner portion of the wall 32.

Because the portion off the aorta 30 in the aortic arch 46 is curved in two dimensions, the actual skew of the velocity profile may be complex. In addition, the branching of the arteries 48, 50, and 52 in this area to the arms and the head influences the blood velocity profile, especially at station 54. Further, wave reflections from these arterial branches will affect the blood velocity profiles near this portion of the ascending aorta.

The velocity profile skew is expected to change during systole, due to the different effects of blood acceleration and deceleration on the velocity profile. Another factor which complicates the flow of blood through the aorta is the transverse movement of the blood which occurs as the aortic wall 32 expands during systole. Because of the complicated nature of the blood flow in the aorta, it is clear that simple estimates of correct sensor placement and/or cardiac output, based, for example, on maximum velocity at a particular aortic station, can be very inaccurate.

Given the variability in human anatomy, it is difficult to predict whether a preset Doppler sample depth resides at a level between stations 34 and 42. If the Doppler sample volume resides at or near level 34, the velocity gradient across the lumen may be too slight to adequately distinguish the center of the lumen by maximization of narrow beam velocity, with the consequence that the wide beam may not be adequately centered. If, on the other hand, the sample depth occurs at or near station 42, manipulation of the transducer to achieve maximization of the velocity in the narrow beam will place the sample volume to the side of the lumen. This could result in uneven insonification of the aorta by the wide beam, and possible failure to place the narrow beam wholly within moving blood.

It has also been suggested that maximization of the velocity in the narrow beam will :result in adequate centering of the ACVF sample volumes in the aorta. The foregoing discussion regarding the complex nature of the aortic velocity profile served to point out the limitations inherent in this approach.

Equations (1) and (2) are used to calculate the velocity profiles at the different phases of the cardiac cycle. The calculated profiles show that the flow is neither parabolic nor plug, but is closer to that of plug flow at the station 33. The flow profile differs from person to person and is a slowly varying function of cardiac cycle.

Figure 4:
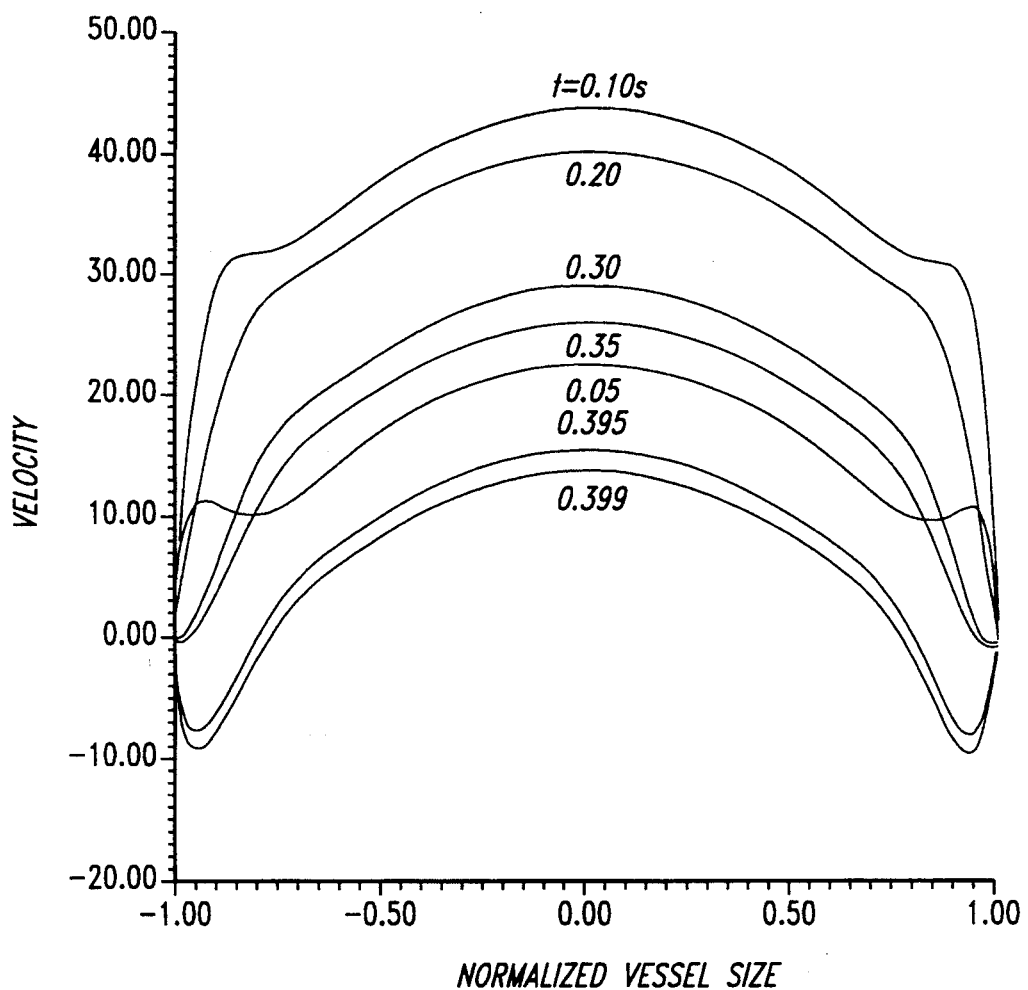
FIG. 4 is a graph of the calculated aortic flow profile versus normalized aorta diameter at different times in the cardiac cycle.

FIG. 4 is a graph Of the calculated aortic flow profile versus normalized aorta diameter at different phases in the cardiac cycle, showing that the velocity profiles are more similar to those of a plug profile than those of a parabolic profile. The spatially averaged mean velocity can be obtained for a known velocity profile and beam profile by $$\bar{V}(t) = \frac{\int_0^{2\pi} d\phi \int_0^R V(\vec{r},t) b(\vec{r}) r \, dr}{\int_0^{2\pi} d\phi \int_0^R b(\vec{r}) r \, dr}, \quad (3)$$

where $V(\vec{r},t)$ is the velocity profile;
$b(\vec{r})$ is the beam profile at a given depth.

Equation (3) is used to calculate the mean velocity waveform for the narrow beam.

Figure 5:
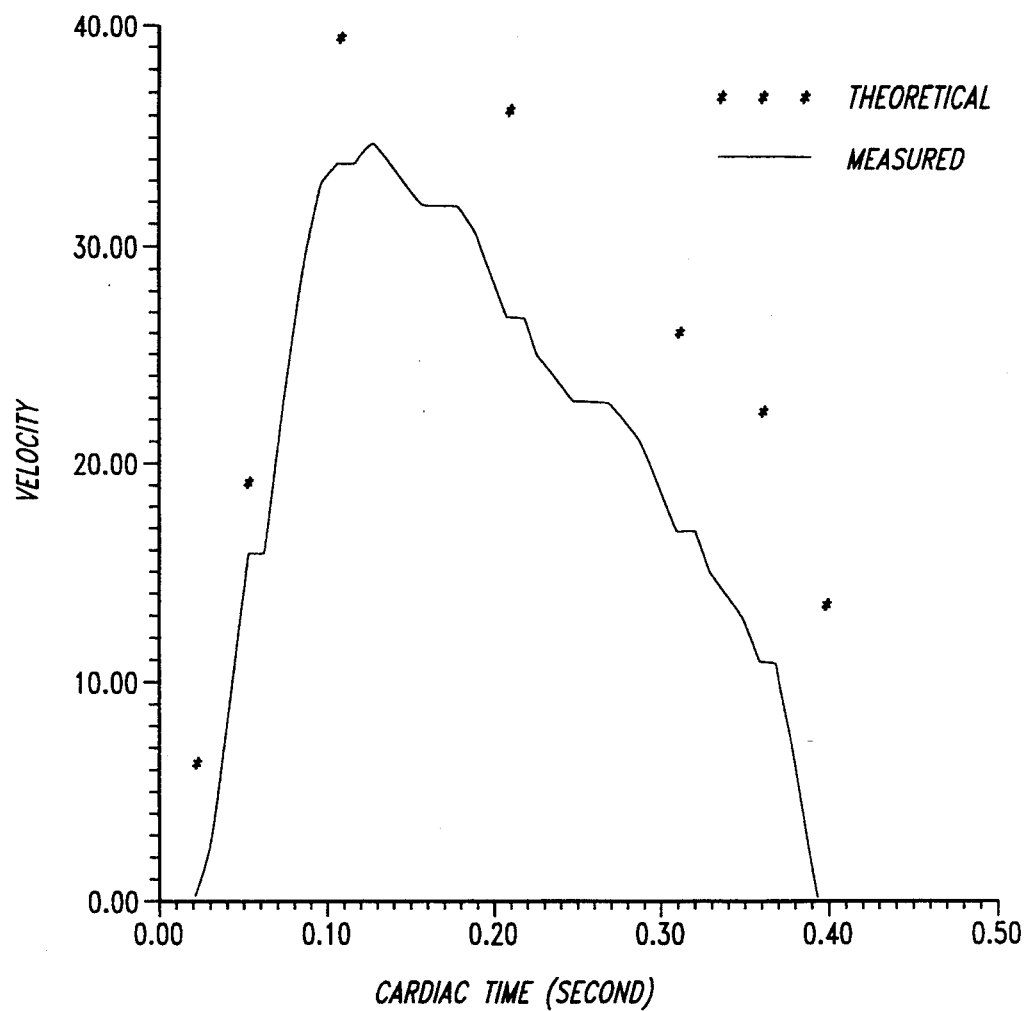
FIG. 5 is a graph of the comparison of the theoretical results and in vivo data.

FIG. 5 is a graph of the comparison of the theoretical mean velocity results and in vivo data as a function of time in the cardiac cycle. These results are consistent with each other even though they do not match perfectly due to several factors. These factors include the fact that the blood flow is not ideal pulsatile flow, the blood vessel is not a straight rigid tube and the contributions from the side lobes of the narrow insonification beam were neglected. Despite all of these factors the theoretical prediction agrees reasonably well with the measured data.

Figure 6C:
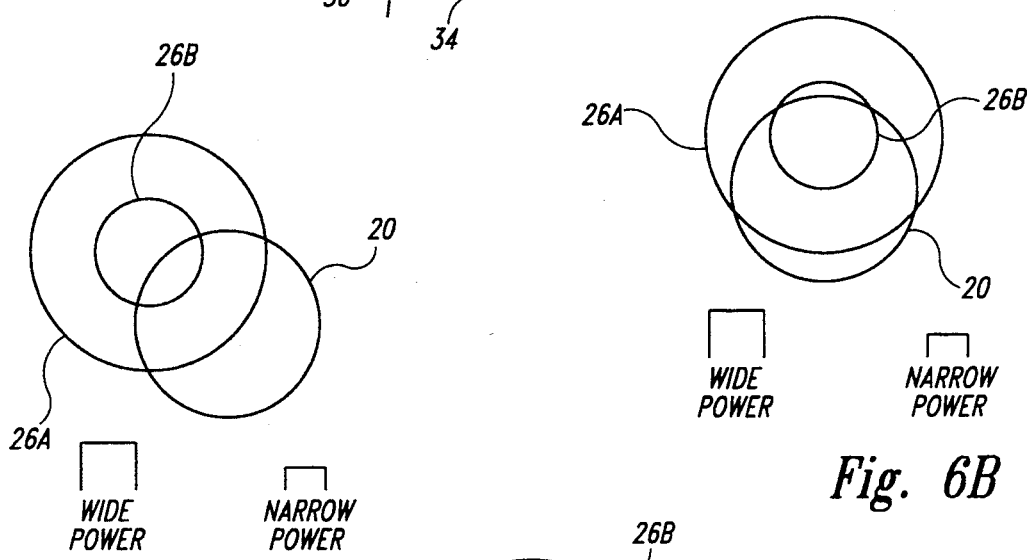
Figure 6C:
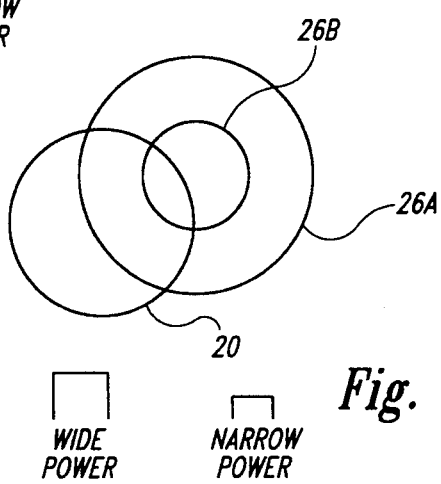

It has been suggested that maximization of the Doppler power in the wide and narrow sample volumes can serve as an adequate signature that the beams are acceptably centered about the aorta. FIGS. 6A–C are schematic representations of the wide and narrow power received as a function of sample volume position. FIGS. 6A–C show, however, that unless the acoustic search is thorough enough to bring the sample volumes through the center of the aorta, maximization of the wide and narrow powers does not necessarily result in the fulfillment of the Hottinger criteria for sample volume placement. Such a search might take place when operating with a apparatus as shown in FIG. 2. It shows that maximum wide and narrow power are achieved without fulfillment of the Hottinger requirements for sample volume placement. As seen in FIGS. 6A and 6C, when an aorta does not encompass either the entire wide or narrow sample volumes, both the wide and narrow power returns are diminished. As shown in FIG. 6B, even when substantially the entirety of the narrow sample volume is encompassed, the wide beam power exceeds that of the narrow beam.

Figure 7A:
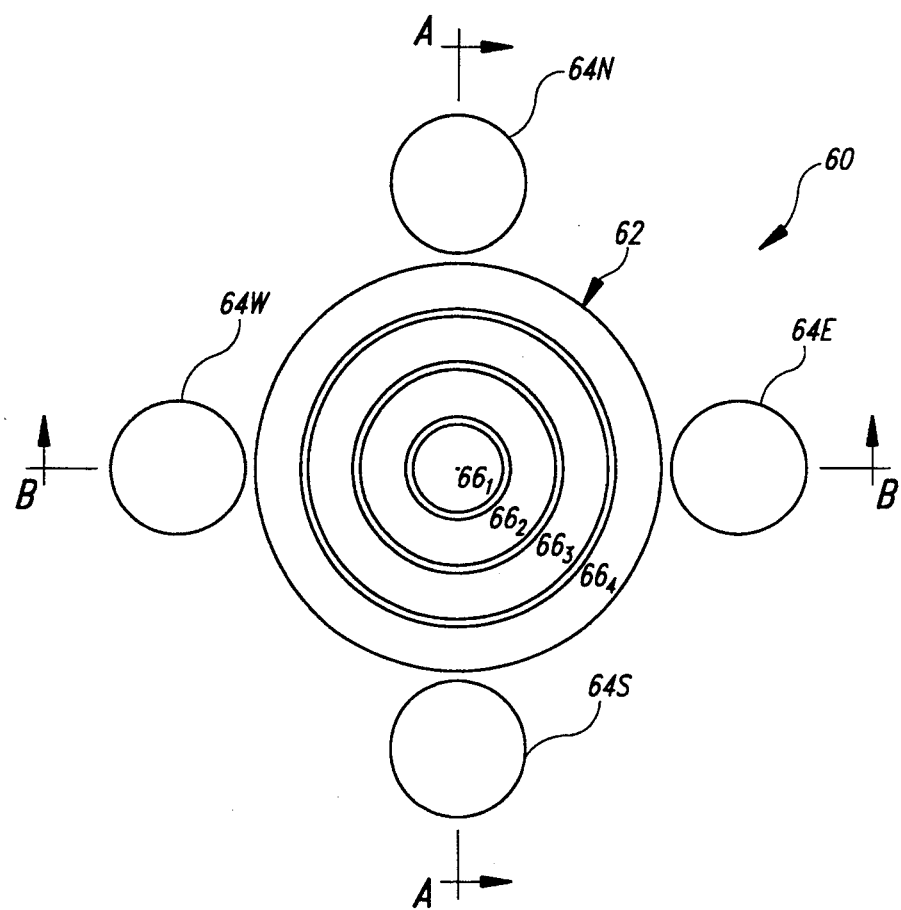
FIG. 7A is a plan view of an ultrasonic device useful in connection with the present invention.
Figure 7B:
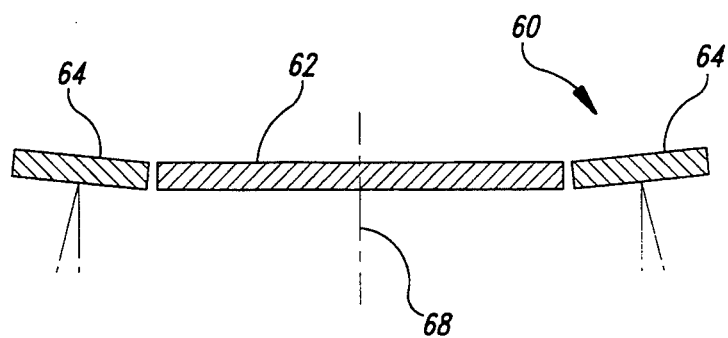
FIG. 7B is an elevation view of the ultrasonic device useful in connection with this invention, as shown in FIG. 7A, taken along either section lines AA or BB.

FIGS. 7A and 7B are, respectively, a plan and an elevation view of an ultrasonic transducer 60 which permits 1) the generation of the wide and narrow sample volumes specified in the Hottinger art, and 2) the independent sampling of Doppler power in each of four quadrants (designated, for convenience, as North, South, East and West) of the wide sample volume. The ultrasonic transducer 60 will be connected to an eight channel, pulsed-Doppler acquisition and processing system (not shown) which will cause the ultrasonic transducer 60 to transmit a series of pulses and receive the returning pulses. The eight channel system can be made according to principles well known by those skilled in the art. The transmitted pulses can consist of between five and fifteen cycles of a carrier frequency chosen from the range of 2 to 4 MHz at a pulse repetition frequency (PRF) of approximately 5 kHz to 40 kHz.

The ultrasonic transducer 60 will, in part, consist of a central four element annular array 62 which will be used to generate and receive the wide and narrow sample volumes described in the Hottinger art. The four circular ultrasonic transducers 64N, 64S, 64E, and 64W, which form a second array surrounding the central array 62 will be used to sense the Doppler power in each quadrant of the wide sample volume. Although the crystals 62 are shown to be 1.8 millimeter circles, they could also be any other convenient size or shape, such as annular segments, as is shown in a second embodiment of the device of the invention.

The central array 62 consists of four elements. Four concentric annular elements, designated $66_1$, $66_2$, $66_3$, and $66_4$, starting from the innermost element, are placed at the center of the central array 62. The diameter of the annular element $66_1$ is approximately 1.50 millimeters. The outside diameter of the annular element $66_2$ is approximately 3.20 millimeters, and is separated from the annular element $66_1$ by approximately 0.15 millimeter. The outside diameter of the annular element $66_3$ is approximately 4.90 millimeters, and is separated from the annular element $66_2$ by approximately 0.15 millimeter. The outside diameter of the annular element $66_4$ is approximately 7.00 millimeters, and is separated from the annular element $66_2$ by approximately 0.15 millimeter.

The circular transducers 64N, 64S, 64E, and 64W of the second array 64 are composed of a conventional piezocomposite material. Each of these elements is centered at a radius of 4.60 millimeters from the center of the central array 62 and has a diameter of 1.8 millimeters. As shown in FIG. 6B, which is taken along either section lines AA or BB of FIG. 6A, the central array 62 is substantially planar and perpendicular to an axis 68, while the transducers 64 in the second array are directed outwardly from the axis 68 at a small angle, such as five degrees. In this way, the ultrasonic fields received by each of the transducers 64 is further separated from the ultrasonic fields received by the other transducers 64 than it would otherwise be.

When using the annular array technology of Fu and Gertzberg in ACVF applications, the width of the wide beam is inversely related to the size of the inner element. In his aforementioned thesis, Evans discussed the width-to-thickness constraints imposed upon ultrasonic transducers constructed from standard piezoelectric materials. In the ACVF device constructed by Evans, the properties of the piezoelectric material that he employed limited the minimum diameter of the central array element to two millimeters. This, in turn, resulted in a wide beam which provided a uniform pressure amplitude in a longitudinal interval of less than three centimeters at a six centimeter sample depth. In terms of sensitivity to Doppler power, the wide beam was uniformly sensitive for a lateral distance of only two centimeters, while many adults' aortas are over three centimeters wide at a depth of six centimeters from the skin surface.

In order to escape from the width-to-thickness constraints described by Evans, the transducers were fabricated out of diced, composite materials. This helps to avoid lateral mode coupling effects and thereby make transducer elements of arbitrary size irrespective of carrier frequency. Accordingly, the transducer produces wide beams which uniformly insonify the largest adult aortas (about 3.5 centimeters in diameters).

The elements of the transducer 60 are defined by an electrode pattern separated by shallow kerfs on the back surface of the piezocomposite material. The kerfs do not exceed 0.25 millimeter in width. Electrically tuned transformers (not shown), which are physically separate from the transducer 60, are respectively connected to each of the elements of the transducer 60. The piezocomposite material can advisably include either quarter-wave matching layers and/or air or air-like backing materials in order to maximize the sensitivity of the transducer 60. The transducer 60 is connected to a conventional handle designed for good access to the suprasternal notch, and appropriate coaxial cables are used to transfer signals to and from the transducer 60. The assembly including the transducer 60 and the handle are made from materials which are unaffected by indefinite immersion (at least 350 hours)in water and aqueous coupling gels at a temperature of 65 Celsius.

Generation and Reception of the Wide Sample Volume:

The sequential array elements are driven simultaneously and out of phase with one another, with variable gain weightings, to generate a uniform wide beam in the far field of the transducer. As disclosed by Nudell, et al. in U.S. patent application Ser. No. 07/417,525, appropriate transducer amplitude characteristics are produced by using the gain and phase settings noted in Table 1. After a suitable time delay (consonant with a seven centimeter sample depth), the Doppler signals received by the inner three elements of the central array 62 will be summed (using the same phase and gain settings as described in Table 1) to permit the calculation of the total Doppler power and mean velocity of blood in the wide sample volume.

TABLE 1

| Element | Gain | Phase (degrees) |
|---------|------|-----------------|
| 1 | 1.000 | 0 |
| 2 | 0.095 | 180 |
| 3 | 0.010 | 0 |
| 4 | 0.000 | — |

There are several practical limitations on wide beam size. It is necessary to make the wide sample volume wide enough to uniformly insonify the largest aortas that will be encountered. However, it is disadvantageous to make the wide sample volume so large as 1) to insonify adjacent arterial lumens such as the pulmonary artery, and 2) to increase the likelihood of troublesome reflections off structures such as the trachea and lungs.

The avoidance of measurement errors due to contamination of the aortic flow signal by Doppler signals from forward moving blood in the pulmonary artery is a major consideration. In most subjects, it is possible to make virtually uncontaminated aortic blood flow measurements. At preferred sample depths (five to seven centimeters for small adult subjects, and six to eight centimeters for large adults), the Doppler sample volume is generally above the main pulmonary artery trunk which runs parallel to the aorta. At these depths, the Doppler sample volume tends to be contiguous with the transversely oriented, right and left pulmonary artery branches. While there may be, in some subjects, a small upward (toward the transducer) movement of blood in the right and left pulmonary branches, the high angle of incidence of this flow relative to the ultrasonic beam generally results in small Doppler shifts which are removed by the wall filter (high-pass) circuitry. Finite amounts of contamination can occur however, and it is obviously desirable to minimize the insonification of the pulmonary artery.

Increasing the wide beamwidth beyond the size of the aorta will serve to lower the ultrasonic intensity in the aorta, and thereby lowers the signal to noise ratio of the device. If, in an attempt to maintain the signal to noise ratio, it is necessary to raise the input energy imposed upon the inner element to compensate for increased beam width, there is the very real risk of exceeding the regulatory limitations placed upon maximum ultrasonic intensity (expressed in watts/centimeters$^2$). This is especially true as the size of the inner transducer element is progressively minimized, as is the skin contact area of the inner element, in order to make progressively wider beams.

When making ACVF measurements on the largest aortas, the practical limitation imposed on the wide beamwidth demand that the operator be able to precisely center the Doppler sample volumes about the aorta.

Generation and Reception of the Narrow Sample Volume:

In order to maximize the pulse repetition frequency of the Doppler system, the narrow sample volume will not be transmitted and received independently of those to the wide sample volume, even though in many cases it is possible to do this without violating the aliasing criteria, which determines a lower limit to the pulse repetition frequency.

Figure 8:
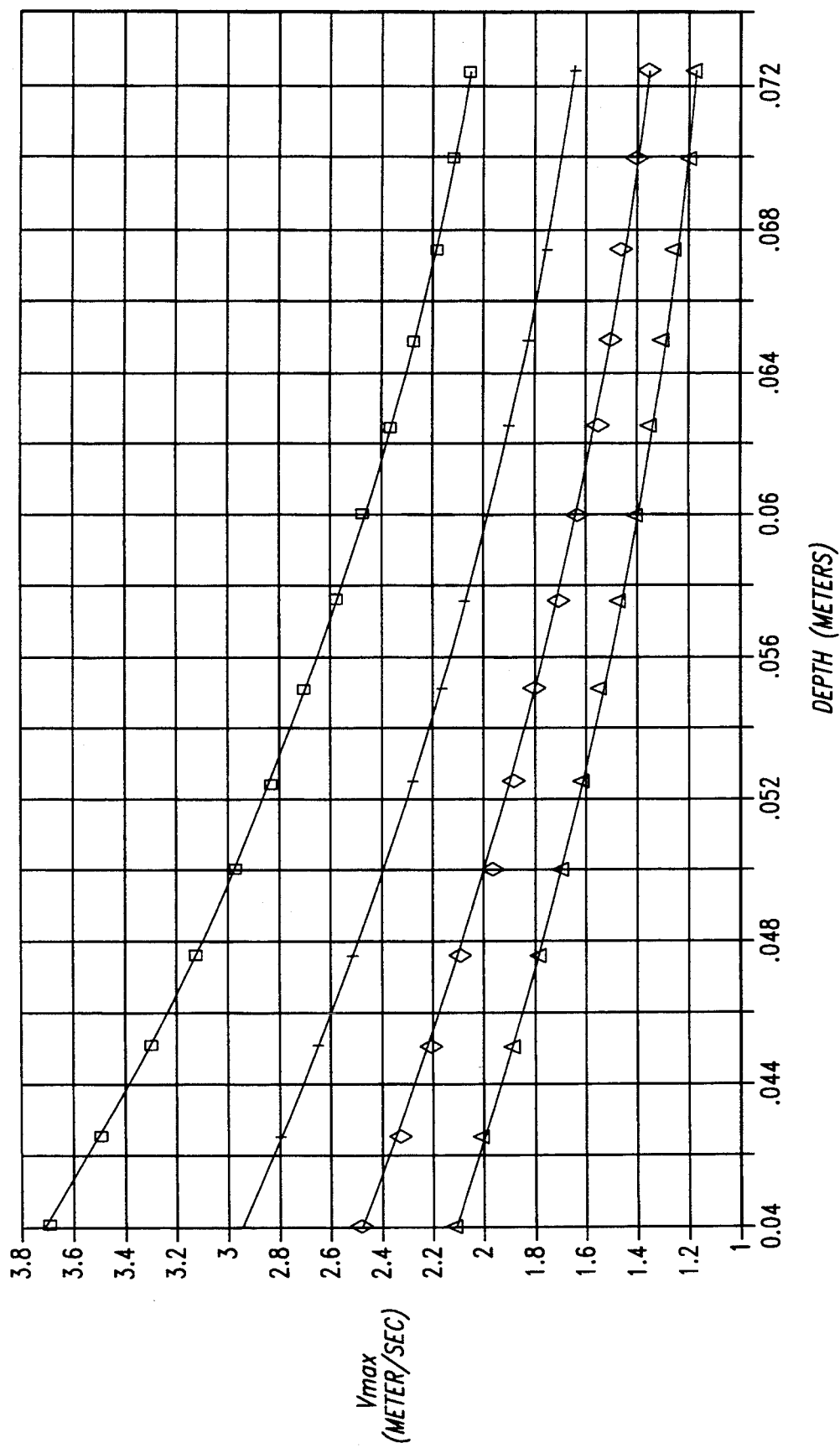
FIG. 8 is a graph of the relationship between sample depth and carrier frequency versus maximum measurable blood velocity for a pulsed Doppler system in human tissue.

FIG. 8 shows the relationship between sample depth and carrier frequency versus maximum measurable blood velocity for a bidirectional pulsed Doppler system in human tissue. FIG. 8 shows that at 2 MHz and a sample depth of six centimeters, it is possible to comfortably measure the anticipated maximum aortic velocities (1–1.5 m/sec). Halving the effective pulse repetition frequency to accommodate independent transmission and reception of the wide and narrow beams would halve the maximum velocity that could be tracked (in the wide or narrow beam) at any given interrogation depth. It is very likely that with a 2 MHz carrier frequency and a sample depth of 5 centimeters, it is possible to transmit the wide and narrow beams independently and still be able to track the maximum aortic velocity without violating the Nyquist aliasing criteria.

Following transmission of the uniform, wide beam, the range gated Doppler signals received by each receive transducer 64 and elements 66$i$ will be summed, with variable gain and equal phase, to effectively generate a narrow Doppler sample volume as described in the Skidmore patent. The settings to produce the wide beam are different from those required to produce the narrow beam. Further, as described in the Hottinger art, the Doppler power ascribable to this narrow sample volume is calculated in order to compensate for variable intersubject ultrasonic attenuation and scattering in order to derive an accurate projected aortic area.

When using the Fu/Gertzberg annular array technology, narrow beam size is inversely related to the diameter of the annular array. Many small subjects, who possess accordingly small aortas, may not be able to tolerate suprasternal transducers with footprints in excess of twelve millimeters. An additional constraint which limits the narrowness of the inner sample volume (given a fixed transducer footprint) is that aliasing considerations may, under some circumstances, preclude the independent transmission and reception of the wide and narrow sample volumes. As a consequence of these two factors, the beamwidth (main lobe) of the narrow sample volume may be in excess of one centimeter at a six centimeter sample depth.

Given the size of the narrow sample volumes that can be achieved, small (0.5 centimeter) misalignments of the narrow beam relative to the center of small aortic lumens (two centimeters diameter) will result in underestimation of narrow power, and hence erroneous estimates of aortic area and cardiac output. (When dealing with the smallest aortas, the wide beam tolerance for misalignment generally exceeds that of the narrow beam.)

Many small adult subjects, who possess accordingly small aortas, may not be able to tolerate suprasternal transducers with footprints in excess of twelve millimeters. An additional constraint which limits the narrowness of the inner sample volume (given a fixed transducer footprint) is that aliasing considerations may, under some circumstances, preclude the independent transmission and reception of the wide and narrow sample volumes, as disclosed in Evans' thesis. As a consequence of these two factors, the main lobe beamwidth of the narrow sample volume may be in excess of one centimeter at a six centimeter sample depth.

Given the size of the narrow sample volumes that can be achieved, small misalignments (of, say, 5 millimeters) of the narrow beam relative to the center of the small aortic lumen will :result in underestimation of narrow power, and hence erroneous estimates of aortic area and cardiac output. According to these arguments, the narrow beam is less affected by misalignment error than is the wide beam.

Figure 9:
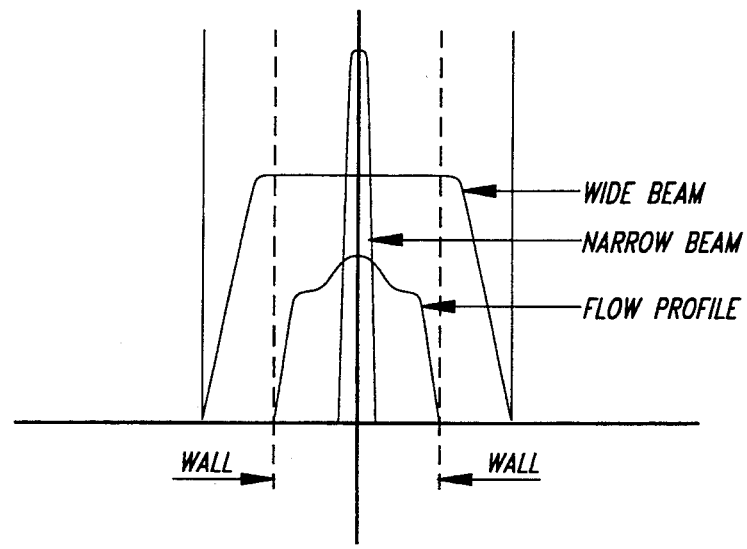
FIG. 9 is graph of the flow profile in a typical aorta and of the beam profiles of the beams of the present invention.

FIG. 9 is a graph of the flow profile in a typical aorta and of the beam profiles of the beams of the present invention. It shows that the flow profile between the lumen walls is wholly contained within the wide beam, while it wholly contains the narrow beam. It also shows that the narrow beam will sample only a small portion of the flow profile and will provide a sensitive indicator to whether the narrow beam is near the maximum of the flow profile.

In ACVF applications, the ability to pick a sample depth with minimum angle of incidence and hence minimum projected cross-sectional area is important given the constraints on wide beam formation enunciated above. Similarly, when using a pulsed, wide,beam Doppler signal to obtain an accurate mean velocity estimate for flow in a vessel, minimization of the angle of incidence and the concomitant underestimation of mean velocity is obviously a desirable goal.

In practice it is necessary to limit the size of the wide beam to that of the largest anticipated aortas. This, in turn, places added importance on centering the wide beam in large aortas, as the theory of operation of ACVF devices calls for Uniform insonification of the target lumen.

Circuit Description

Figure 10:
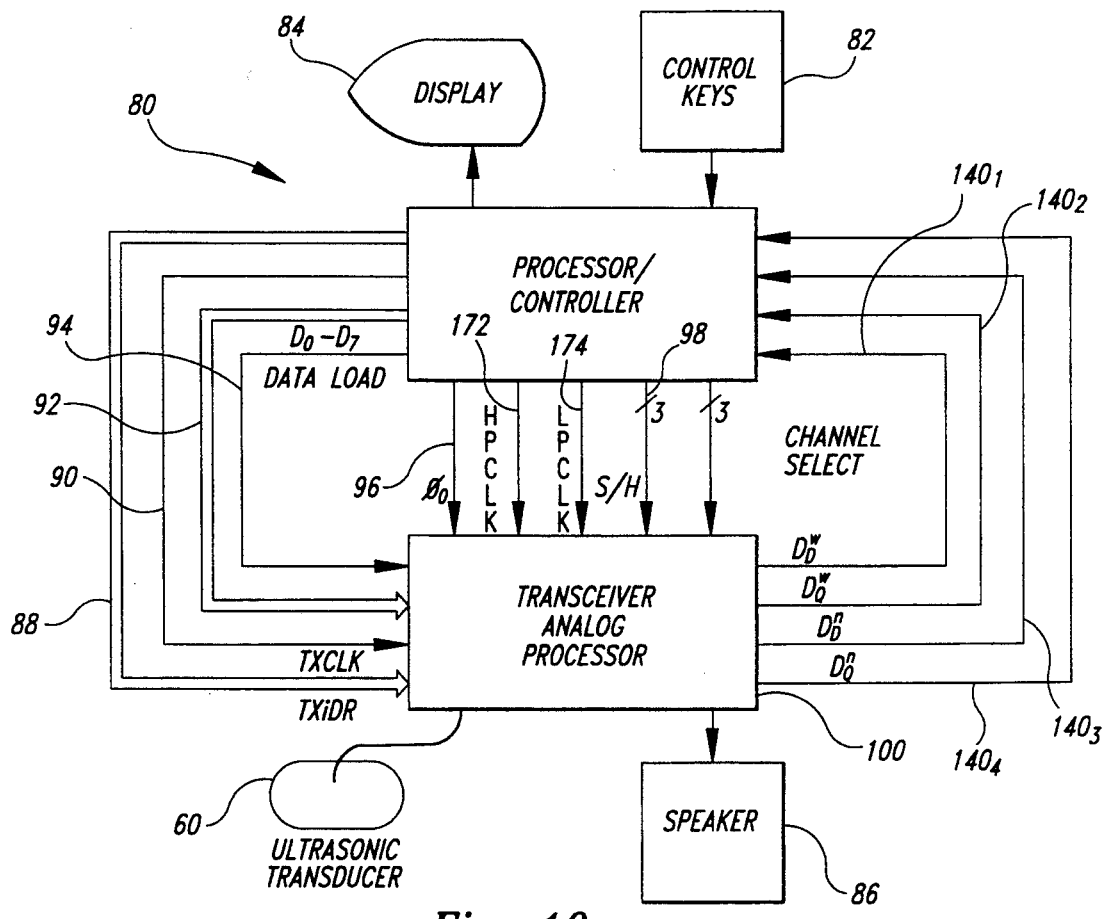
FIG. 10 is a schematic diagram of an apparatus for implementing the method of the invention.

FIG. 10 is a schematic diagram of an apparatus or implementing the method of the invention. The apparatus includes a processor/controller 80, a transceiver analog processor 100, and interconnecting data lines. The processor/controller 80 can take the form of a personal computer that has been programmed to receive commands from control keys 82, to send commands to the transceiver analog processor 100, and to receive Doppler signals from the transceiver analog processor 100. The processor/controller 80 also includes a conventional display 84 for displaying the results of the program being run by the processor/controller 80. The transceiver analog processor 100 also receives signals from the ultrasonic transducer 60 and can be caused to produce audio signals which may be played on a standard speaker 86.

The processor/controller 80, under control of its program, produces transmitter drive signals on the bus 88. The transmitter drive signals prescribe the amplitude of signals that will be transmitted by the four annular elements $61_i$ in the ultrasonic transducer 60. The amplitude of the transmitted signals can be specified by an operator through the conventional control keys 82. The processor/controller 80 also transmits a transmit clock signal to the transceiver analog processor 100. The transmit clock signal determines the time when the transmitted pulses are to be transmitted by the ultrasonic transducer 60. The pulse repetition frequency of the transmissions produced by the ultrasonic transducer 60 is controlled by the frequency of the transmit clock signal, and may be specified by the operator through the control keys 82. The processor/controller 80 also produces data on the data bus 92 and data load signals on the data load bus 94. The data carried on the data bus 92 include phase signals used to define each transmitted pulse, to specify attenuation quotients used by the ultrasonic transducer when is receives the reflected ultrasonic energy in the body, and specifies which signal (if any) will be sent to the speaker 86 by the transceiver analog processor 100. The processor controller 80 also produces a phase shift signal on line 96. The phase shift signal specifies a phase shift which is used by a conventional RF amplifier and demodulator in the receiver circuitry of the transceiver analog processor 100. The processor/controller 80 also produces the sample and hold signal on the line 98. The sample and hold signal is delayed relative to the transmit clock signal On line 90 by a period of time which defines the interrogation depth from which the reflected ultrasonic signals are received.

The transceiver analog processor 100 produces direct and quadrature signals received from the wide and narrow beams produced by the ultrasonic transducer, and sends them, via lines $142_i$, to the processor/controller 80. As will be described subsequently, the processor/controller 80 will receive the Doppler signals from the transceiver analog processor 100 and produce values for the mean and maximum velocities i measured by the ultrasonic transducer 60. These values are used in criteria which determine whether the ultrasonic transducer 60 is properly placed relative to the ascending aorta 20. If the ultrasonic transducer 60 is not properly placed, the processor/controller 80 can produce an indication on the display 84, prompting the operator to continue to manipulate the ultrasonic transducer 60 until satisfactory placement of the ultrasonic transducer 60 is achieved. If the Doppler signals produced by the transceiver analog processor 100 satisfy the criteria of the invention, however, the processor/controller 80 further processes these signals to produce a value of the flow through the ascending aorta 20. The value of this flow can be shown on the display 84 under the control i of the processor/controller 80. The processor/controller 80 can provide further sophisticated programming including, but not limited to, fast Fourier transform (FFT) or other frequency domain analysis.

Figure 11A:
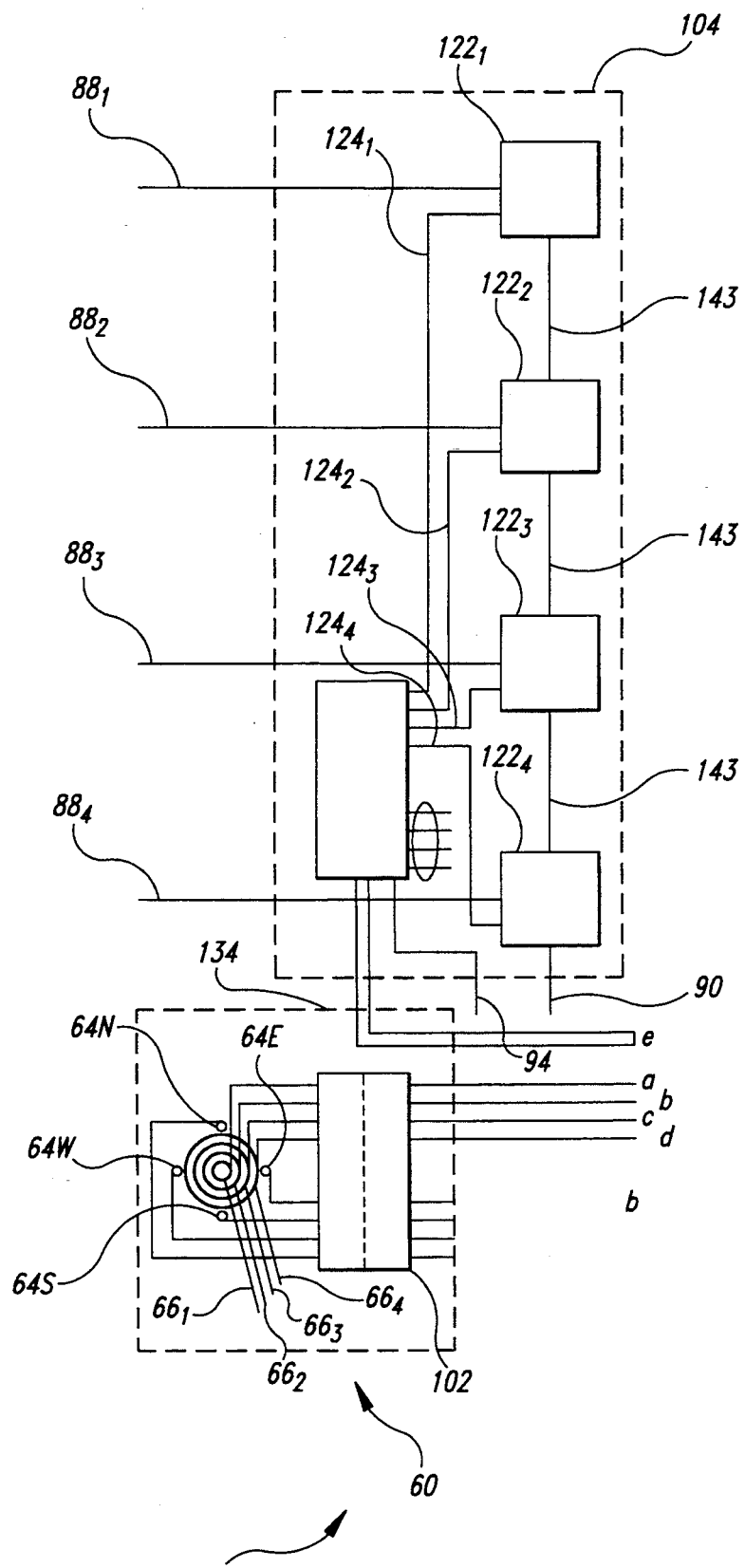
FIGS. 11A-C comprise a schematic diagram of the transceiver analog circuit of the apparatus of FIG. 10.
Figure 11B:
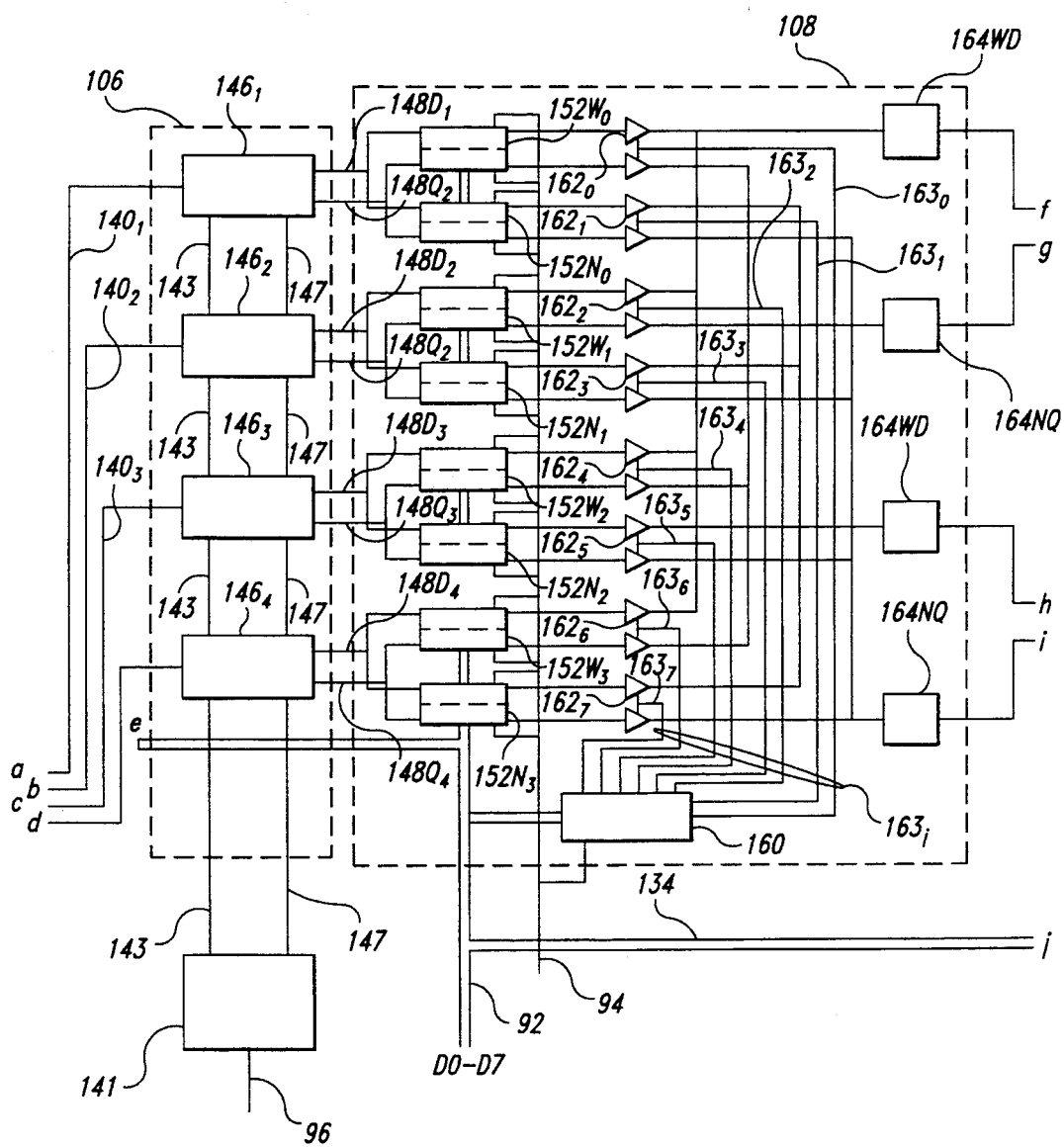
Figure 11C:
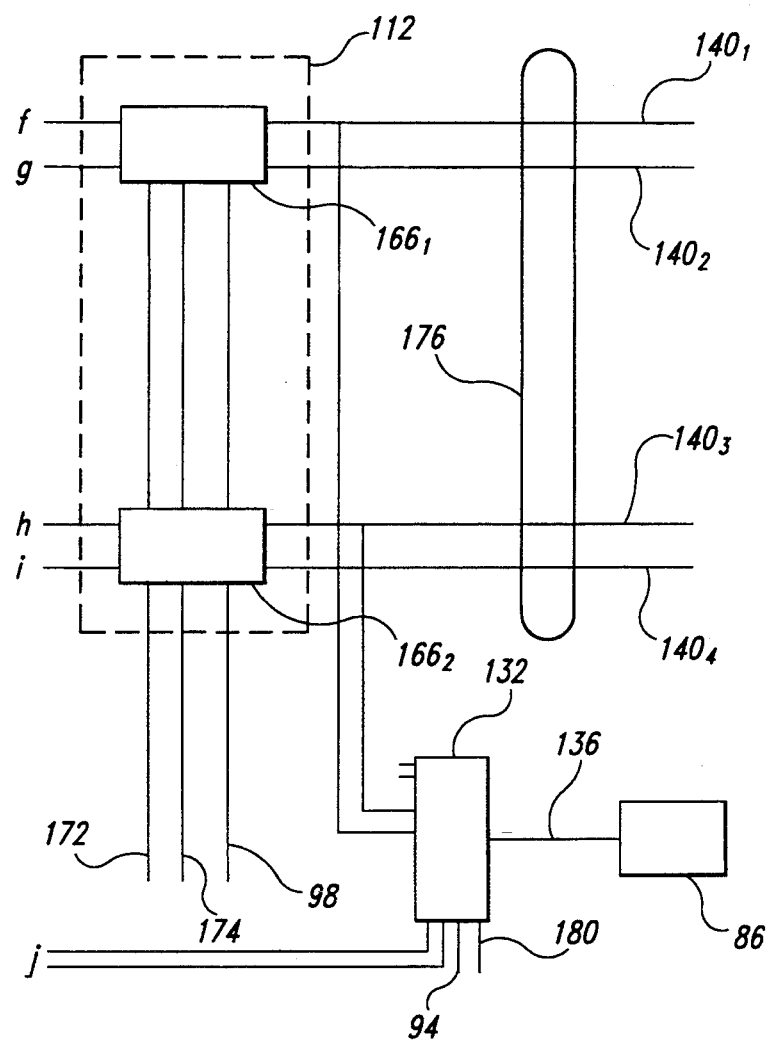

FIGS. 11A–C comprise a schematic diagram of the transducer analog circuit of the apparatus of FIG. 10. Circuit 100 can cause the transducer 60 to transmit appropriate pulsed signals through the first array 62. Circuit 100 can also process the received transducer signals and produce both wide and narrow receive Doppler signals. Further, circuit 100 can produce signals indicating the relative powers and velocities measured by the aiming transducers 64 in order to specify the direction in which the transducer 60 should be moved in order to be optimally placed with respect to the aorta.

The transducer 60 is connected to the circuit 100 through a connector 102 which permits the ready replacement of one embodiment of the transducer 60 for another. The circuit 100 consists of a transmitter section 104, receiver circuitry 106, transmit and receive coefficient generators 108 and 110, and signal processor circuits 112 and 114.

The transmitter section 104, comprising four transmit amplifiers $122_i$ (for i=1, ..., 4), receives transmit level signals through lines $120_i$, which are connected to the processor/controller 80. Each of the amplifiers $122_i$ also receives a phase signal $124_i$ from a transmit phase control latch 126. The transmit phase control latch 126 receives information from which it produces the phase signals through the data lines 128 at a time designated through the data load signal line 94. The transmit phase control latch 126 also transmits phase control data to the coefficient generators 108 and 110, and an audio signal to an audio select amplifier 132 through a data bus 134. The audio select amplifier 132 is connected to the external speaker 86 through a speaker line 136.

In response to a signal delivered from the processor/controller 80 over the transmit clock line 138, each of the amplifiers $122_i$ produces a pulse having a predetermined frequency amplitude and phase over a bidirectional transmit/receive line $140_i$ which is connected to a separate one of the concentric annular elements $66_i$ through connector 102. The transmitted energy is supplied at an RF frequency (e.g., 2 MHz) by a conventional phase-shifted ultrasonic source 141 through a line 143.

In response to the pulses transmitted toward a patient's ascending aorta through the suprasternal notch by the concentric annular elements $66_i$, the concentric annular elements $66_i$ receive reflected ultrasonic energy. The energy received through the ultrasonic transducers $66_i$ is respectively sent, via bidirectional lines $142_i$ to the RF amplifiers and demodulators $146_i$. The RF amplifiers and demodulators $146_i$ are included in the receiver circuitry 106.

The amplifier section of each of the RF amplifiers and demodulators $146_i$ is connected to a conventional phase-shifted ultrasonic energy source 141 through the interconnecting line 143 which interconnects all of the RF amplifiers and demodulators 146. The ultrasonic energy source 141 produces ultrasonic energy at the frequency of the transmitted energy. The demodulator section of each of the RF amplifiers and demodulators $146_i$ is similarly connected to the ultrasonic energy source 141 through the interconnecting line 147 which provides ultrasonic energy having a phase shift of $phi_O$ degrees. The signals produced by the RF amplifiers and demodulators $146_i$ are the direct and quadrature components of the Doppler modulated frequency signals corresponding to the velocity of blood measured by each of the elements in the transducer 60. The quadrature signals differ from the direct signals by a phase of 90 degrees. This information can be used by the processor/controller 80 to determine the direction of the blood flow.

The direct and quadrature signals produced by the RF amplifiers and demodulators $146_i$ are respectively sent over lines $148D_i$ and $148Q_i$ to conventional attenuators in the coefficient generator 108. The signals sent over lines $148D_1$ and $148Q_1$ are both sent to attenuators 152W0 and 152N0. The signals sent over lines $148D_2$ and $148Q_2$ are both sent to attenuators 152W1 and 152N1. The signals sent over lines $148D_3$ and $148Q_3$ are both sent to attenuators 152W2 and 152N2. The signals sent over lines $148D_4$ and $148Q_4$ are both sent to attenuators 152W3 and 152N3. The attenuators 152Wi provide the proper attenuation to the received Doppler signals to produce the wide beam Doppler signals, while the attenuators 152Ni produce the narrow beam Doppler signals.

The attenuators 152 are each connected to the data bus 134 which transmits appropriate eight-bit weighting data to the attenuator which is selected by the processor/controller 80 through the 27-bit DATA LOAD signal on line 156. This signal is also received on line 156 by the receive phase control latch 160 which receives transmit phase control signals from the transmit phase control latch 126 through the data bus 134, under the control of the controller/processor 80, and produces the values of eight phases, $P_j$, for $j = 0, ..., 7$. The receive phase control latch sends the phases $P_j$, $j=0, ..., 7$ to the phase shifters $162_j$ through the lines $163_j$. The phases $P_j$, for $j=0, ..., 7$, are respectively used to adjust the phase of the signals produced by attenuators 152W0, 152N0, 152W1, 52N1, 152W2, 152N2, 152W3, and 152N3.

The phase-shifted signals produced by phase-shifting the direct signals $148D_k$ through the phase shifters $160_0$, $160_2$, $160_4$, and $160_6$ are added in adder 164WD. Also, the phase-shifted signals produced by phase-shifting the quadrature signals $148Q_k$ through the phase shifters $160_0$, $160_2$, $160_4$, and $160_6$ are added in adder 164WQ. Further, the phase-shifted signals produced by phase-shifting the direct signals $148D_k$ through the phase shifters $160_1$, $160_3$, $160_5$, and $160_7$ are added in adder 164ND. Finally, the phase-shifted signals produced by phase-shifting the quadrature signals $148Q_k$ through the phase shifters $160_1$, $160_3$, $160_5$, and $160_7$ are added in adder 164NQ. The adders 164 are located in the coefficient generator 108.

The signals produced by the coefficient generator 108 are processed by the signal processor 112, which includes sample-and-hold and band-pass filter units $166_1$ and $166_2$. The sample-and-hold and band-pass filter unit $166_1$ operates on the direct and quadrature signals respectively produced by the adders 164WD and 164WQ. Similarly, the sample-and-hold and band-pass filter unit $166_2$ operates on the direct and quadrature signals respectively produced by the adders 164ND and 164NQ.

The sample-and-hold and band-pass filter units $166_1$ and $166_2$ each receive sample-and-hold timing signals on the three-bit sample-and-hold line 98 from the processor/controller 80. The timing signals determine when the sample-and-hold and band-pass filter units $166_1$ and $166_2$ are activated. The time interval between the transmit clock signal on the line 90 and timing signals on the line 98 determines the interrogation depth. Also, the band-pass filter units operate on the Doppler signals to reduce any spread in their frequency caused by variations in the blood flow velocity across the corresponding sample volume.

The signals produced by the signal processor 112 and 114 are transmitted through the lines $140_j$ to the processor/controller 80 for further signal-processing circuitry as described below.

Method of the Invention

Since blood flow only occurs inside the blood vessel, the parameters associated with flow such as the velocity should be able to provide some useful information about the relative location of the insonification beam and the flow profile. For the two beam transducer Doppler instrument, assume that the beam and flow profile are perfectly lined-up. Then the following relationships between the velocities exist:

$$V_{max}^W \sim V_{max}^N;$$

$$V_{Max}^N \sim V_{mean}^N;$$

$$V_{mean}^W \sim V_{mean}^N;$$

where $V_{max}^W$ is the maximum velocity measured by the wide beam, $V_{mean}^W$ is the spatially averaged velocity measured by the wide beam, $V_{max}^N$ is the maximum velocity measured by the narrow beam.

Next, if the beam is off the center of the flow profile, the following relationships should be true (see FIG. 9):

$$V_{max}^W > V_{max}^N;$$

The value of $$\frac{V_{mean}^N}{V_{max}^N}$$

should decrease compared with that under perfect conditions.

Combining the above relationships, we used the following criteria to identify the valid beat from a series of heart beats contained in one measuring trial:

$$97.5\% \leq \frac{V_{max}^W}{V_{max}^N} \leq 100\%; \quad (1)$$

$$\frac{V_{mean}^W}{V_{max}^W} \geq 60\%; \quad (2)$$

$$\frac{V_{mean}^N}{V_{max}^N} \geq 70\%; \quad (3)$$

$$V_{mean}^W \leq V_{mean}^N. \quad (4)$$

If a beat satisfies all the above conditions, it is identified as a valid beat. The above numerical criteria were chosen for no specific reason rather a preliminary test value. They can be modified to either stricter or more relaxed criteria.

The invention will also be useful for aligning simple Doppler velocimeters with various biological vessels. The ability to center Doppler sample volumes of defined shape within biological vessels will allow for more precise and stable blood velocity measurements, as is described in U.S. Pat. No. 4,796,634, issued to Huntsman et al.

It may prove that 2-D echo image estimates of aortic diameter will be more readily available as echo imagers become more ubiquitous in the critical care environment. If this is the case, a widebeam, pulsed Doppler velocimeter (as opposed to flowmeter) which is aimed at the aorta from the suprasternal notch could provide the estimate of the mean aortic velocity integral that is necessary to make cardiac output calculations. Errors in cardiac output measurements could be expected to result from the velocity underestimations that occur due to the angle of incidence of the ultrasound beam. This error can be minimized if the present technique is used to identify the sample depth at which the angle of incidence is lowest. The current invention would be very useful in providing an aiming mechanism for such a device.

To confirm the operation of the invention, the maximum velocity, mean velocity and the total backscattered power were obtained by both the wide and narrow beams for a total of nineteen healthy male and female subjects. The body sizes range from 1.5 m to 1.9 m and the aortic diameters range from 21 mm to 32 mm obtained from MRI images. Theoretically the backscattered power from the red blood cells is proportional to the instantaneous vessel cross-sectional area. The total power received by a transducer is the zero's moment of the power spectrum and is given by $$P = \int(f)df \propto \alpha(z)\sigma I(z)A_n,$$

where z = depth where the measurement is taken,
$\alpha(z)$ = attenuation,
$\sigma$ = volumetric scattering coefficient of the blood,
I(z) = beam sensitivity,
$A_n$ = projected area of vessel lumen.

The ratio of the total received power by the wide and narrow beam is given by:

$$\frac{P_W}{P_N} = k(z)A_W;$$

where $P_w$ is the total received power by the wide beam,
$P_n$ is the total received power by the narrow beam,
k(z) is a constant which is a function of the depth z,
$A_w$ is the lumen area of the wide beam.

The multichannel pulsed Doppler workstation described in the foregoing was used to collect the $P_W$, $P_n$, $V_{mean}^n$, $V_{max}^n$, $V_{mean}^W$, and $V_{max}^W$ for eighteen volunteers. The Doppler power is the integrated power through the whole cardiac cycle and the $V_{mean}$ and $V_{max}$ are the values at peak systole. One clinical trial is defined as the whole process: the operator puts the transducer on the suprasternal notch and moves it around until the position at which the best audio signal and a reasonable amount of power is found; the transducer is held steady at that position to collect data; the transducer is removed from the subject. There are total of eight trials and each trial has about 18 heart beats for each patient. The data of all other trials were postprocessed using the algorithm to pick the valid beats whose ratio of $P_w$ and $P_N$ are averaged.

Figure 12:
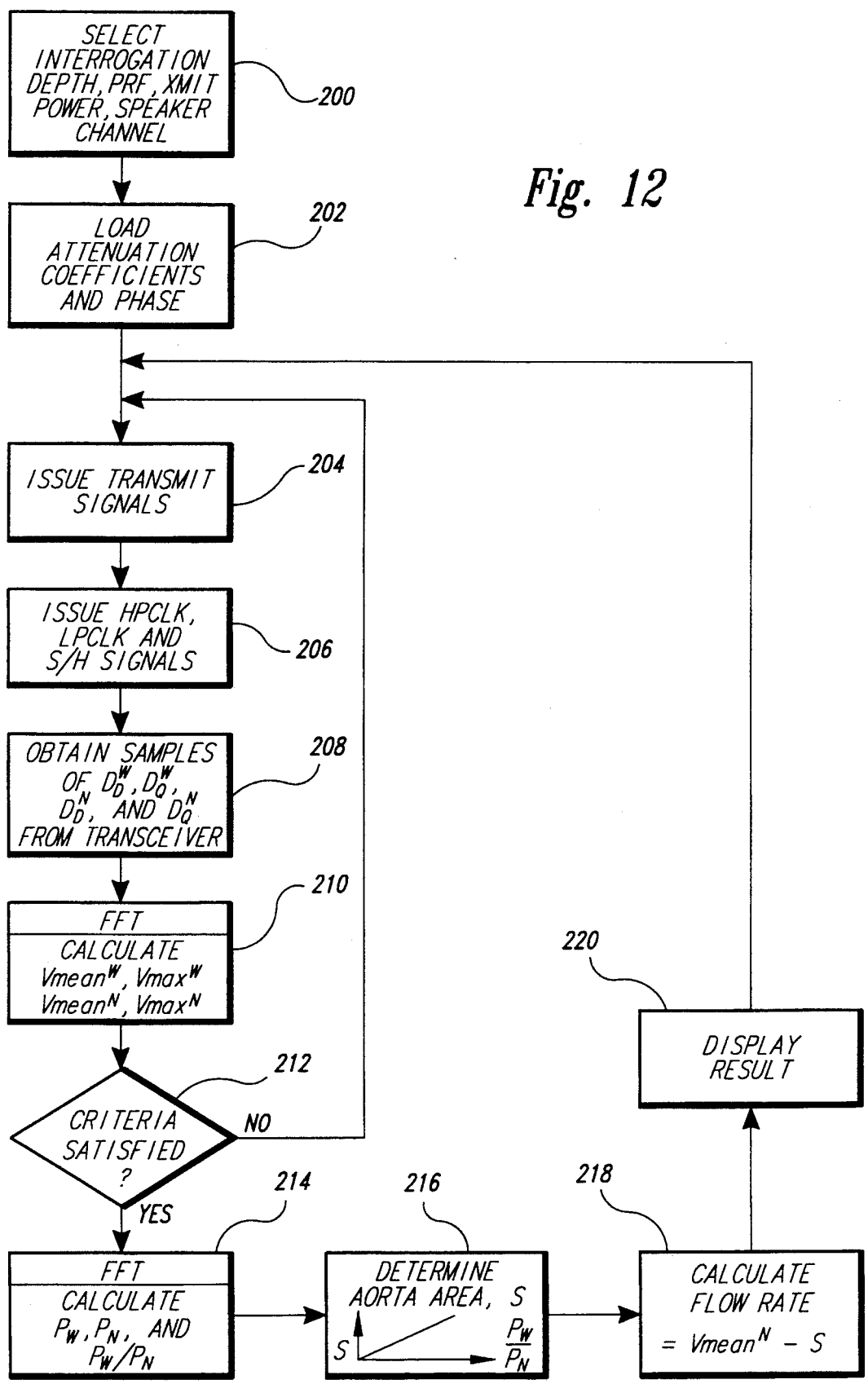
FIG. 12 is a flow chart of the program in the processor/controller of the apparatus of FIG. 10.

FIG. 12 is a flow chart of the program in the processor/controller 80 of the apparatus of FIG. 10. According to the program, the operator can choose such parameters as transmit power produced by the ultrasonic transducer 60, pulse repetition frequency, and which channel (if any) of the output signals on the lines 140$_i$ the operator wishes to listen to, as well as the interrogation depth the operator is interested in. Following this initialization step 200, the program loads the phases and attenuation coefficients required by the transmit amplifiers 122$_i$ and the attenuation coefficients required by the RF amplifiers and demodulators 146$_i$, onto the data bus 92 (step 202).

The program in the programmer/controller 80 then issues ultrasonic amplitude signals and transmit clock signals on data bus 88 and clock line 90, respectively (step 204). After a prescribed period of time, the processor/controller sends high and low pass information to the sample-and-hold and band-pass filters 166$_i$ to tailor their band-pass response as desired, and then issues the sample and hold signal on the line 98, after a predetermined time delay. This time delay is a measure of the interrogation depth requested by the operator (step 206). In step 208, the program in the programmer/controller 80 obtains samples of the signals containing direct and quadrature Doppler information from the wide and narrow beams of the ultrasonic transducer 60. A fast Fourier transform (FFT) is performed on the received signals to produce the mean and maximum velocities in the signals on the lines 140$_i$. If desired, the phase shift between the direct and quadrature signals can be used to determine whether the velocity is positive (i.e., toward the ultrasonic transducer 60) or negative (i.e., away from the ultrasonic transducer 60). Based on the values produced by the step 210, the decision block 212 calculates the ratios of $$\frac{V^w_{max}}{V^n_{max}}, \frac{V^w_{mean}}{V^w_{max}}, \text{ and } \frac{V^n_{mean}}{V^n_{max}}.$$

These ratios are compared to constants to discern when the ultrasonic transducer 60 is appropriately oriented relative to the ascending aorta 20. These constants have been empirically determined to provide the criteria with the desired ability. At present, the ratio of $$\frac{V^w_{max}}{V^n_{max}}$$

should be between 0.975 and 1.000, the value of $$\frac{V^w_{mean}}{V^w_{max}}$$

should be greater than 0.600, and the value of $$\frac{V^n_{mean}}{V^n_{max}}$$

should be greater than or equal to 0.7. If desired, an additional condition that can be required is that $V_{mean}^w$ must be less than or equal to $V_{mean}^n$.

If the velocity data do not satisfy the validity criteria in the decision block 212, the program returns to the block 204.

If the data do satisfy the inequality criteria, the program in the programmer/controller 80 processes the velocity data received on the lines 140$_i$ to calculate the total power received by the wide and narrow beams ($P_w$ and $P_n$, respectively). Their ratio $$\left(\frac{P_w}{P_n}\right)$$

is calculated in step 214, the aortic area(s) can be determined by a known linear relationship between the power ratio and aortic area (step 216), and the flow rate through the ascending aorta 20 can be calculated by multiplying the aortic area(s) by the mean velocity as measured by the narrow beam ($V_{mean}^n$), in step 218. The result can be displayed on the display 84 connected to the processor/controller 80 (step 220). Thereafter, the program in the processor/controller 80 returns to step 204, where the processor/controller 80 issues further pulse transmit signals.

While the detailed description above has been expressed in terms of a specific example, those skilled in the art will appreciate that many other circuits could be used to accomplish the purpose of the disclosed inventive apparatus. Accordingly, it can be appreciated that various modifications of the above-described embodiments may be made without departing from the spirit and the scope of the invention. Therefore, the spirit and the scope of the present invention are to be limited only by the following claims.

I claim:

1. Apparatus for aiming a sensor for detecting the flow of a fluid through a vessel at an interrogation depth in a body, comprising:

transmit means for transmitting a pulse of energy into the body;

first receive means for receiving the energy reflected in a wide area from an interrogation depth and producing a first receive signal in response thereto and for receiving the energy reflected in a narrow area from the interrogation depth and producing a second receive signal in response thereto, the narrow area being encompassed by the wide area; and means for processing the first receive signal and producing a mean wide velocity value ($V_{mean}^W$) and a maximum wide velocity value ($V_{max}^W$) therefrom, for processing the second receive signal and producing a mean narrow velocity value ($V_{mean}^n$) and a maximum narrow velocity value ($V_{max}^n$) therefrom, and for processing $V_{mean}^W$, $V_{max}^W$, $V_{mean}^n$, and $V_{max}^n$ and producing an indication signal indicating whether the narrow beam is confined within the vessel at the interrogation depth and the wide beam confines the vessel at the interrogation depth.

2. The apparatus of claim 1 wherein the processing means produces an indication signal indicating that the narrow beam is confined within the vessel at the interrogation depth and the wide beam confines the vessel at the interrogation depth when the following conditions are met:

$K_1 \leq V_{max}W/V_{max}^N \leq K_2$;

$V_{mean}^W/V_{max}^W \geq K_3$; and $V_{mean}^N/V_{max}^N \geq K_4$.

3. The apparatus of claim 2 wherein $K_1=0.975$, $K_2=1.000$, $K_3=0.600$, and $K_4=0.700$.

4. The apparatus of claim 1 wherein the processing means produces an indication signal indicating that the narrow beam is confined within the vessel at the interrogation depth and the wide beam confines the vessel at the interrogation depth when the following conditions are met:

$K_1 \leq V_{max}^W/V_{max}^N \leq K_2$;

$V_{mean}^W/V_{max}^W \geq K_3$;

$V_{mean}^N/V_{max}^N \geq K_4$; and $V_{mean}^W \leq V_{mean}^N$.

5. The apparatus of claim 4 wherein $K_1=0.975$, $K_2=1.000$, $K_3=0.600$, and $K_4=0.700$.

6. Apparatus for aiming a sensor for detecting the flow of a fluid through a vessel at an interrogation depth in a body, comprising:
   transmit means for transmitting a pulse of energy into the body;
   first receive means for receiving the energy reflected in a wide area from an interrogation depth and producing a first receive signal in response thereto;
   second receive means for receiving the energy reflected in a narrow area from the interrogation depth and producing a second receive signal in response thereto, the narrow area being encompassed by the wide area;
   means for processing the first receive signal and producing a mean wide velocity value ($V_{mean}^W$) and a maximum wide velocity value ($V_{max}^W$) therefrom;
   means for processing the second receive signal and producing a mean narrow velocity value ($V_{mean}^N$) and a maximum narrow velocity value ($V_{max}^N$) therefrom; and
   means for processing $V_{mean}^W$, $V_{max}^W$, $V_{mean}^N$, and $V_{max}^N$ and producing an indication signal indicating whether the narrow beam is confined within the vessel at the interrogation depth and the wide beam confines the vessel at the interrogation depth.

7. The apparatus of claim 6 wherein the means for processing the velocity values produces an indication signal indicating that the narrow beam is confined within the vessel at the interrogation depth and the wide beam confines the vessel at the interrogation depth when the following conditions are met:

$K_1 \leq V_{max}W/V_{max}^N \leq K_2$;

$V_{mean}^W/V_{max}^W \geq K_3$; and $V_{mean}^N/V_{max}^N \geq K_4$.

8. The apparatus of claim 7 wherein $K_1=0.975$, $K_2=1.000$, $K_3=0.600$, and $K_4=0.700$.

9. The apparatus of claim 6 wherein the means for processing the velocity values produces an indication signal indicating that the narrow beam is confined within the vessel at the interrogation depth and the wide beam confines the vessel at the interrogation depth when the following conditions are met:

$K_1 \leq V_{max}^W/V_{max}^N \leq K_2$;

$V_{mean}^W/V_{max}^W \geq K_3$;

$V_{mean}^N/V_{max}^N \geq K_4$; and $V_{mean}^W \leq V_{mean}^N$.

10. The apparatus of claim 9 wherein $K_1=0.975$, $K_2=1.000$, $K_3=0.600$, and $K_4=0.700$.

11. Apparatus for aiming a sensor for detecting blood flow through a blood vessel at an interrogation depth in a body, the blood flow being caused by a repetitive motion of a heart, comprising:
    transmit means for transmitting a pulse of energy into the body at a predetermined time within the repetitive motion of the heart;
    first receive means for receiving the energy reflected in a wide area from an interrogation depth and producing a first receive signal in response thereto;
    second receive means for receiving the energy reflected in a narrow area from the interrogation depth and producing a second receive signal in response thereto, the narrow area being encompassed by the wide area;
    means for processing the first receive signal and producing a mean wide velocity value ($V_{mean}^W$) and a maximum wide velocity value ($V_{max}^W$) therefrom;
    means for processing the second receive signal and producing a mean narrow velocity value ($V_{mean}^N$) and a maximum narrow velocity value ($V_{max}^N$) therefrom; and
    means for processing $V_{mean}^W$, $V_{max}^W$, $V_{mean}^N$, and $V_{max}^N$ and producing a first indication signal indicating whether the narrow beam is confined within the blood vessel at the interrogation depth and the wide beam confines the blood vessel at the interrogation depth.

12. The apparatus of claim 11 wherein the means for processing the velocity values produces an indication signal indicating that the narrow beam is confined within the vessel at the interrogation depth and the wide beam confines the vessel at the interrogation depth when the following conditions are met:

$K_1 \leq V_{max}W/V_{max}^N \leq K_2$;

$V_{mean}^W/V_{max}^W \geq K_3$; and $V_{mean}^N/V_{max}^N \geq K_4$.

13. The apparatus of claim 12 wherein $K_1=0.975$, $K_2=1.000$, $K_3=0.600$, and $K_4=0.700$.

14. The apparatus of claim 11 wherein the means for processing the velocity values produces an indication signal indicating that the narrow beam is confined within the vessel at the interrogation depth and the wide beam confines the vessel at the interrogation depth when the following conditions are met:

$$K_1 \leq V_{max}^W/V_{max}^N \leq K_2;$$

$$V_{mean}^W/V_{max}^W \geq K_3;$$

$$V_{mean}^N/V_{max}^N \geq K_4; \text{ and}$$

$$V_{mean}^W \leq V_{mean}^N.$$

15. The apparatus of claim 14 wherein $K_1=0.975$, $K_2=1.000$, $K_3=0.600$, and $K_4=0.700$.

16. The apparatus of claim 11, wherein the transmit means transmits a plurality of the pulses of energy at predetermined times within the repetitive motion of the heart.

17. The apparatus of claim 16 wherein the means for processing the values produces a corresponding series of first indication signals, further comprising means for producing a second indication signal upon the first occurrence of a first indication signal indicating that the narrow beam is confined within the blood vessel at the interrogation depth and the wide beam confines the blood vessel at the interrogation depth within each repetitive motion of the heart.

18. The apparatus of claim 17 wherein the means for processing the velocity values produces a first indication signal indicating that the narrow beam is confined within the vessel at the interrogation depth and the wide beam confines the vessel at the interrogation depth when the following conditions are met:

$$K_1 \leq V_{max}^W/V_{max}^N \leq K_2;$$

$$V_{mean}^W/V_{max}^W \geq K_3;$$

$$V_{mean}^N/V_{max}^N \geq K_4; \text{and}$$

$$V_{mean}^W \leq V_{mean}^N.$$

19. The apparatus of claim 18 wherein $K_1=0.975$, $K_2=1.000$, $K_3=0.600$, and $K_4=0.700$.

20. The apparatus of claim 16 wherein the means for processing the velocity values produces an indication signal indicating that the narrow beam is confined within the vessel at the interrogation depth and the wide beam confines the vessel at the interrogation depth when the following conditions are met:

$$K_1 \leq V_{max}W/V_{max}^N \leq K_2;$$

$$V_{mean}^W/V_{max}^W \geq K_3; \text{ and}$$

$$V_{mean}^N/V_{max}^N \geq K_4.$$

21. The apparatus of claim 20 wherein $K_1=0.975$, $K_2=1.000$, $K_3=0.600$, and $K_4=0.700$.

22. A method for aiming a sensor for detecting the flow of a fluid through a vessel at an interrogation depth in a body, comprising the steps of:
(a) transmitting a pulse of energy into the body;
(b) receiving the energy reflected in a wide area from an interrogation depth and producing a first receive signal in response thereto;
(c) receiving the energy reflected in a narrow area from the interrogation depth and producing a second receive signal in response thereto, the narrow area being encompassed by the wide area;
(d) processing the first receive signal and producing a mean wide velocity value ($V_{mean}^W$) and a maximum wide velocity value ($V_{max}^W$) therefrom;
(e) processing the second receive signal and producing a mean narrow velocity value ($V_{mean}^N$) and a maximum narrow velocity value ($V_{max}^N$) therefrom; and
(f) processing $V_{mean}^W$, $V_{max}^W$, $V_{mean}^N$, and $V_{max}^N$ and producing an indication signal indicating whether the narrow beam is confined within the vessel at the interrogation depth and the wide beam confines the vessel at the interrogation depth.

23. The method of claim 22, further comprising the step of (g) producing an indication signal indicating that the narrow beam is confined within the vessel at the interrogation depth and the wide beam confines the vessel at the interrogation depth when the following conditions are met:

$$K_1 \leq V_{max}W/V_{max}^N \leq K_2;$$

$$V_{mean}^W/V_{max}^W \geq K_3; \text{and}$$

$$V_{mean}^N/V_{max}^N \geq K_4.$$

24. The method of claim 23, wherein $K_1=0.975$, $K_2=1.000$, $K_3=0.600$, and $K_4=0.700$.

25. The method of claim 22, further comprising the step of (g) producing an indication signal indicating that the narrow beam is confined within the vessel at the interrogation depth and the wide beam confines the vessel at the interrogation depth when the following conditions are met:

$$K_1 \leq V_{max}^W/V_{max}^N \leq K_2;$$

$$V_{mean}^W/V_{max}^W \geq K_3;$$

$$V_{mean}^N/V_{max}^N \geq K_4; \text{and}$$

$$V_{mean}^W \leq V_{mean}^N.$$

26. The method of claim 25 wherein $K_1=0.975$, $K_2=1.000$, $K_3=0.600$, and $K_4=0.700$.

27. A method for aiming a sensor for detecting blood flow through a blood vessel at an interrogation depth in a body, the blood flow being caused by a repetitive motion of a heart, comprising the steps of:
(a) transmitting a pulse of energy into the body at a predetermined time within the repetitive motion of the heart;
(b) receiving the energy reflected in a wide area from an interrogation depth and producing a first receive signal in response thereto;
(c) receiving the energy reflected in a narrow area from the interrogation depth and producing a second receive signal in response thereto, the narrow area being encompassed by the wide area;
(d) processing the first receive signal and producing a mean wide velocity value ($V_{mean}^W$) and a maximum wide velocity value ($V_{max}^W$) therefrom;
(e) processing the second receive signal and producing a mean narrow velocity value ($V_{mean}^N$) and a maximum narrow velocity value ($V_{max}^N$) therefrom; and
(f) processing $V_{mean}^W$, $V_{max}^W$, $V_{max}^N$, and $V_{max}^N$ and producing a first indication signal indicating whether the narrow beam is confined within the blood vessel at the interrogation depth and the wide beam confines the blood vessel at the interrogation depth.

28. The method of claim 27 wherein step (a) includes transmitting a plurality of the pulses of energy at predetermined times within the repetitive motion of the heart.

29. The method of claim 27, further comprising the step of (g) producing an indication signal indicating that the narrow beam is confined within the vessel at the interrogation depth and the wide beam confines the vessel at the interrogation depth when the following conditions are met:

$$K_1 \leq V_{max}{}^W/V_{max}{}^N \leq K_2;$$

$$V_{mean}{}^W/V_{max}{}^W \geq K_3; \text{ and}$$

$$V_{mean}{}^N/V_{max}{}^N \geq K_4.$$

30. The method of claim 29 wherein $K_1=0.975$, $K_2=1.000$, $K_3=0.600$, and $K_4=0.700$.

31. The method of claim 27, further comprising the step of (g) producing an indication signal indicating that the narrow beam is confined within the vessel at the interrogation depth and the wide beam confines the vessel at the interrogation depth when the following conditions are met:

$$K_1 \leq V_{max}{}^W/V_{max}{}^N \leq K_2;$$

$$V_{mean}{}^W/V_{max}{}^W \geq K_3;$$

$$V_{mean}{}^N/V_{max}{}^N \geq K_4; \text{ and}$$

$$V_{mean}{}^W \leq V_{mean}{}^N.$$

32. The method of claim 31 wherein $K_1=0.975$, $K_2=1.000$, $K_3=0.600$, and $K_4=0.700$.

33. The method of claim 31, wherein step (a) includes transmitting a plurality of the pulses of energy within the repetitive motion of the heart, and further comprising the steps of:

(g) producing a series of first indication signals corresponding to the plurality of pulses; and (h) producing a second indication signal upon the first occurrence of a first indication signal indicating that the narrow beam is confined within the blood vessel at the interrogation depth and the wide beam confines the blood vessel at the interrogation depth within each repetitive motion of the heart.

* * * * *